US006218553B1

(12) United States Patent
Ojima

(10) Patent No.: US 6,218,553 B1
(45) Date of Patent: Apr. 17, 2001

(54) PROCESS FOR THE PREPARATION OF TAXANE DERIVATIVES AND β-LACTAM INTERMEDIATES THEREFOR

(75) Inventor: Iwao Ojima, Port Jefferson, NY (US)

(73) Assignee: The State University of New York at Stony Brook, Stony Brook, NY (US)

( * ) Notice: Subject to any disclaimer, the term of this patent is extended or adjusted under 35 U.S.C. 154(b) by 0 days.

(21) Appl. No.: 09/516,019

(22) Filed: Feb. 29, 2000

Related U.S. Application Data

(62) Division of application No. 08/481,205, filed on Jun. 7, 1995, now abandoned, which is a continuation of application No. 08/363,610, filed on Feb. 2, 1995, now abandoned, which is a continuation of application No. 08/011,922, filed on Feb. 1, 1993.

(51) Int. Cl.$^7$ .................................................. C07D 305/14
(52) U.S. Cl. ........................................... 549/510; 549/511
(58) Field of Search ..................................... 549/510, 511

(56) References Cited

U.S. PATENT DOCUMENTS 5,466,834 * 11/1995 Holton ................................. 549/510

* cited by examiner

Primary Examiner—Ba K. Trinh
(74) Attorney, Agent, or Firm—Finnegan, Henderson, Farrabow, Garrett, & Dunner, L.L.P.

(57) ABSTRACT

Taxol (I) is a complex deterpene which is currently considered the most exciting lead in cancer chemotherapy. Taxol possesses high cytotoxicity and strong antitumor activity against different cancers which have not been effectively treated by existing antitumor drugs. However, taxol has a problem with solubility in aqueous media, which may impose some serious limitation in its use. Taxotére (III) seems to have antitumor activity superior to taxol with better bioavailability. Taxotére has a modified taxol structure with a modified C-13 side chain. This fact strongly indicates that modification on the C-13 side chain would provide a new series of taxol and Taxotére analogues which may have higher potency, better bioavailability and less unwanted toxicity. The present invention provides efficient and practical methods for the syntheses of Taxotére and its analogues through β-lactam intermediates and their coupling with baccatin III.

8 Claims, No Drawings

PROCESS FOR THE PREPARATION OF TAXANE DERIVATIVES AND β-LACTAM INTERMEDIATES THEREFOR

This is a division of application Ser. No. 08/481,205, filed Jun. 7, 1995, now abandoned which is a continuation of Ser. No. 08/383,610, filed Feb. 2, 1995, now abandoned which is a continuation of Ser. No. 08/011,922, filed Feb. 1, 1993, now abandoned all of which are incorporated herein by reference.

FIELD OF THE INVENTION

The present invention relates to a process for the preparation of taxoid(s) including TAXOTÉRE and its analogs and the β-lactam intermediates useful in this process.

BACKGROUND OF THE INVENTION

Taxol (I) is a complex diterpene which is currently considered the most exciting lead in cancer chemotherapy. Taxol possesses high cytotoxicity and strong antitumor activity against different cancers which have not been effectively treated by existing antitumor drugs. For example, taxol is currently in phase III clinical trial for advanced ovarian cancer, phase II for breast cancer, and phase I for lung cancers, colon cancer and acute leukemia.

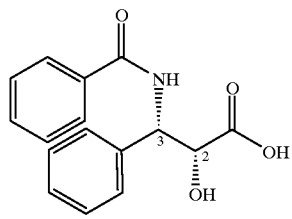
(II)

It is known that the C-13 side chain of taxol, ie., N-benzoyl-(2R,3S)-3-phenylisoserine (III) moiety, is crucial for the strong antitumor activity of taxol. (Senilh et al., *C. R. Séances Acad. Sci. Ser.* 2 1984, 299, 1039; Guéritte-Voegelein et al., *Tetrahedron*, 1986, 42, 4451, and Mangatal et al., *Tetrahedron*, 1989, 45, 4177; Guéritte-Voegelein et al. *J. Med. Chem.* 1991, 34, 992; and Swindell et al., *J. Med. Chem.* 1992, 35, 145; Mathew, A. E. Et al., *J. Med. Chem.* 1992, 35, 145). Moreover, some modification of the C-13 side chain can provide a new series of taxol analogs which may have higher potency, better bioavailability and less unwanted toxicity, as exemplified by the discovery of TAXOTÉRE (II).

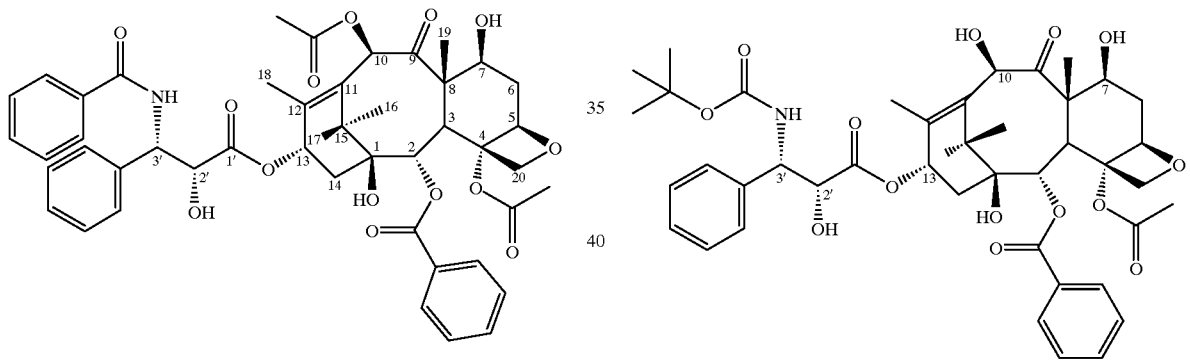

Although taxol is an extremely important "lead" in cancer chemotherapy, taxol has a problem with solubility in aqueous media, which may impose some serious limitation in its use. It is common for improved drugs to be derived from naturally occurring lead compounds. In fact, French researchers, Potier, Guéritte-Voegelein, Guénard et al. have discovered that a modification of the C-13 side chain of taxol brought about a new anticancer agent which seems to have antitumor activity superior to taxol with better bioavailability. This synthetic compound was named "TAXOTÉRE (II)", which has t-butyoxycarbonyl instead of benzoyl on the amino group of (2R,3S)-phenylisoserine moiety at the C-13 position and a hydroxyl group instead of acetoxy group at C-10. [Colin, M. et al. Eur. Pat. Appl. EP25,738 (1988)]. Taxotére is currently in phase II clinical trial in both United States and Europe. TAXOTÉRE has been synthesized by a semisynthetic process, including a coupling of N-tert-butoxycarbonyl-(2R,3S)-3-phenylisoserine with 10-deacetylbaccatin III with proper protecting groups. (Denis, J. N. recently reported (Commercon, A. et al., *Tetrahedron Letters*, 1992, 33 5185).

Accordingly, the development of an efficient method which can be applied to various analogs of taxol and TAXOTÉRE and analogs thereof, i.e., a method having flexibility and wide applicability, is extremely important and of current demand. It has been shown that such a new and efficient method with flexibility can be developed by using enantiomerically pure β-lactams as key-intermediates [Ojima, I. et al., *J. Org. Chem.*, 1991, 56, 1681; Ojima et al., *Tetrahedron*, 1992, 48, 6985; Holton, R. A., Eur. Patent Appl. EP 400,971 (1990)].

Lithium chiral ester enolate-imine cyclocondensation strategy has been applied to the asymmetric synthesis of the side chain of taxol via a (3R,4S)-3-hydroxy-4-phenylazetidin-2-one (IV) as the key-intermediate. (Ojima, I. et al., *J. Org. Chem.*, 1991, 56, 1681; Ojima et al., *Tetrahedron*, 1992, 48, 6985)

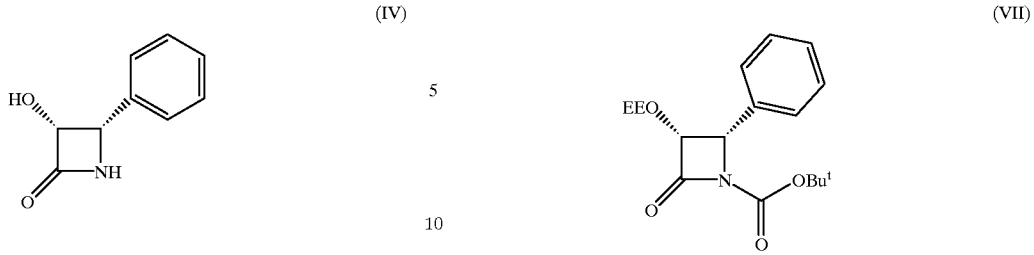

(IV)

(VII)

Based on this protocol, the side chain can be obtained in 3 steps in high yield with virtually 100% e.e. (Ojima, I. et al. *J. Org. Chem.* 1991 56, 1681). Recently, it was found that 1-benzoyl-(3R,4S)-3-(1-ethoxyethoxy)-4-phenylazetidin-2-one (V), readily derived from the hydroxy-β-lactam (IV), served as the key-intermediate for the synthesis of taxol [Holton, R. A. Eur. Pat. Appl. EP 400,971 (1990)]. Therefore, this β-lactam intermediate serves as the key-intermediate for both coupling methods.

It is believed that this may be due to the lack of reactivity of the 1-tert-butoxycarbonyl-β-lactam (VII) toward the c-13 hydroxyl group of a protected baccatin III (VI or VIII) under the conditions used by Holton. The lack of reactivity may be ascribed to the substantially weaker electron-withdrawing ability of tert-butoxycarbonyl group than that of benzoyl group.

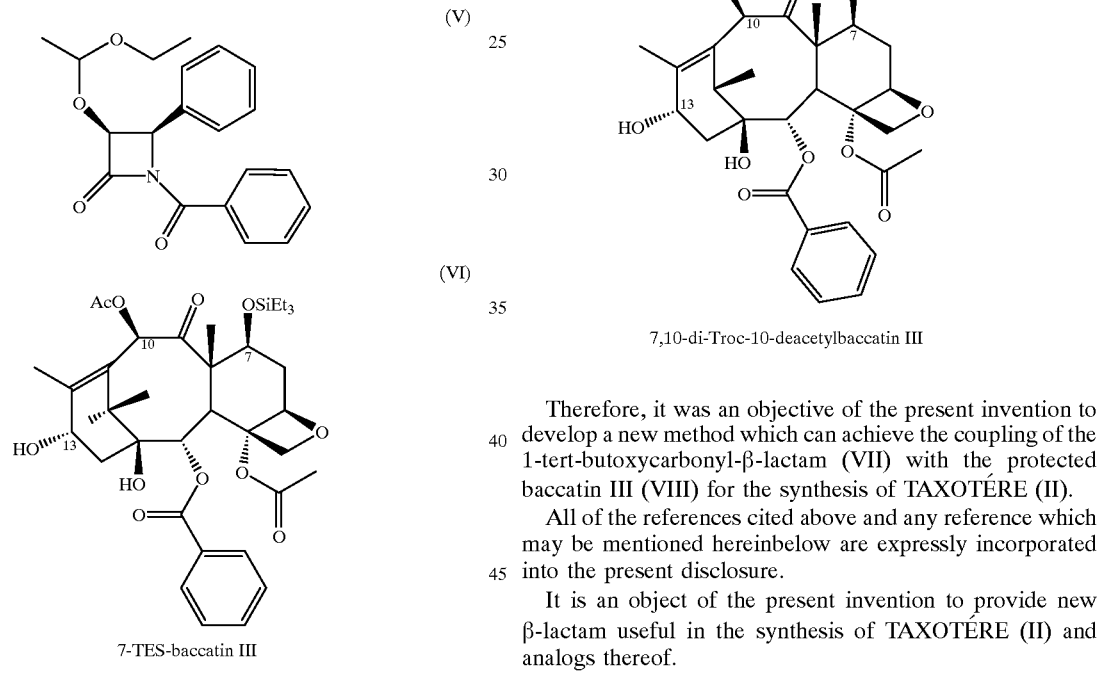

7-TES-baccatin III 7,10-di-Troc-10-deacetylbaccatin III

In the published European application to Holton (hereinafter Holton), the β-lactam intermediate (V) was obtained through tedious optical resolution of the racemic cis-3-hydroxy-β-lactam. According to Holton's procedure, the coupling of the β-lactam (V) with 7-triethylsilylbaccatin III (VI) (7-TES-baccatin III) proceeds at 25° C. in the presence of dimethylaminopyridine (DMAP) and pyridine for 12 hours to give protected taxol in 92% yield, which was deprotected with ~.5% hydrochloric acid in ethanol at 0° C. to afford taxol in ca. 90% yield.

However, the Holton procedure did not work at all when 1-tert-butoxycarbonyl-(3R,4S)-3-(1-ethoxylethoxy)-4-phenylazetidin-2-one (VII) was used for the attempted synthesis of TAXOTÉRE (II) by the present inventors.

Therefore, it was an objective of the present invention to develop a new method which can achieve the coupling of the 1-tert-butoxycarbonyl-β-lactam (VII) with the protected baccatin III (VIII) for the synthesis of TAXOTÉRE (II).

All of the references cited above and any reference which may be mentioned hereinbelow are expressly incorporated into the present disclosure.

It is an object of the present invention to provide new β-lactam useful in the synthesis of TAXOTÉRE (II) and analogs thereof.

It is further object of the present invention to provide a new coupling method for the syntheses of TAXOTÉRE (II) and analogs thereof.

SUMMARY OF THE INVENTION

A β-lactam of the formula (IX)

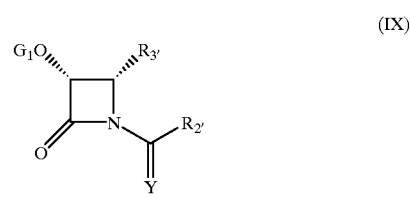

in which $R_2$, represents an RO-, RS- or RR'N- in which R represents an unsubstituted or substituted straight chain or branched alkyl, alkenyl or alkynyl, cycloalkyl, heterocycloalkyl, cycloalkenyl, heterocycloalkenyl, carbocyclic aryl or heteroaryl, wherein substituents bearing one or more active hydrogens such as hydroxyl, amino, mercapto and carboxyl groups are protected; R' is a hydrogen or R as defined above; R and R' can be connected to form a cyclic structure; Examples of $R_1$, include methoxy, ethoxy, isopropoxy, tert-butoxy, neopentyloxy, cyclohexyloxy, allyloxy, propargyloxy, adamantyloxy, phenyoxy, 4-methoxyphenoxy, 2-fluorophenoxy, 4-methoxycarbonylphenoxy, methylthio, ethylthio, isopropylthio, tert-butylthio, neopentylthio, cyclohexylthio, phenylthio, 3,4-dimethoxyphenylthio, methylamino, ethylamino, isopropylamino, tert-butylamino, neopentylamino, cyclohexylamino, dimethylamino, pyrrolidino, piperidino and morpholino group.

$R_3$, represents an unsubstituted or substituted straight chain or branched alkyl, alkenyl or alkynyl radical, an unsubstituted or substituted cycloalkyl, or cycloalkenyl radical, an unsubstituted or substituted aryl radical wherein substituents bearing one or more active hydrogens such as hydroxyl, amino, mercapto and carboxyl groups are protected; Examples of $R_3$, include phenyl, 4-methoxylphenyl, tolyl, 3,4-dimethoxylphenyl, 4-fluorophenyl, 4-trifluoromethylphenyl, 4-chlorophenyl, 4-bromophenyl, naphthyl, cyclohexyl, cyclohexylmethyl, 2-phenylethenyl, 2-phenylethyl, benzyl, neopentyl, tert-butyl, isobutyl, isopropyl, allyl and propargyl;

$G_1$ represents a hydrogen or a hydroxyl protecting group such as methoxymethyl (MOM), methoxylethyl (MEM), 1-ethoxyethyl (EE) benzyloxymethyl, β-trimethylsilylethoxyl)methyl, tetrahydropyranyl, 2,2, 2-trichloroethoxylcarbonyl (Troc), tert-butoxycarbonyl (t-BOC), 9-fluorenylmethoxycarbonyl (Fmoc) 2,2,2-trichloroethoxymethyl, trimethylsilyl, triethylsilyl, dimethylethylsilyl, dimethyl(t-butyl)silyl, diethylmethylsilyl, dimethylphenylsilyl and diphenylmethylsilyl;

Y is oxygen or sulfur.

The present inventors investigated the β-lactam coupling reaction with protected Baccatin III in detail and found that the coupling could be achieved by increasing the nucleophilicity of the 13-hydroxyl group of a protected baccatin III (VI or VIII) through transformation of the hydroxyl group to the corresponding metal alkoxide. Such a C-13 metal alkoxide of a baccatin III was readily generated by reacting the baccatin III (VI or VIII) with an alkali or alkaline earth metal base. The finding is the basis of the present invention. The method of the present invention not only enables the coupling of the β-lactam (VII) and its derivatives and analogs with a protected baccatin III, but also requires only a stoichiometric amount of the β-lactams. The latter makes a sharp contrast with the Holton procedure for taxol synthesis which needs 5–6 equivalents of the more reactive β-lactam (V). Moreover, the coupling reactions of the present invention proceed very smoothly and complete typically within 30 minutes at −30°–0° C.

The present invention also relates to a process for the preparation of taxane derivatives of the formula (X)

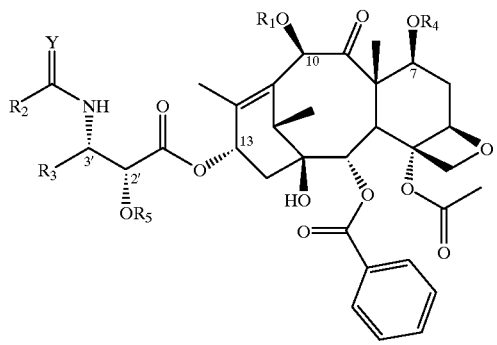

in which $R_1$ represents a hydrogen atom or an acyl or an alkyl or an alkenyl or an alkynyl or carbocyclic aryl or a heteroaryl radical or a hydroxyl protecting group ($G_1$ defined above);

$R_2$ represents an RO, RS- or RR'N- in which R represents an unsubstituted or substituted straight chain or branched alkyl, alkenyl or alkynyl, cycloalkyl, heterocycloalkyl, cycloalkenyl, heterocycloalkenyl, carbocyclic aryl or heteroaryl; R' is a hydrogen or R as defined above; R and R' can be connected to form a cyclic structure;

Y is oxygen or sulfur;

$R_3$ represents an unsubstituted or substituted straight chain or branched alkyl, alkenyl radical, an unsubstituted or substituted cycloalkyl, cycloalkenyl radical or an unsubstituted or substituted carbocyclic aryl radical;

$R_4$ represents a hydrogen or an acyl radical or an unsubstituted or substituted straight chain or branched alkyl, alkenyl or alkynyl radical, an unsubstituted or substituted cycloalkyl, heterocycloalkyl, cycloalkenyl or heterocycloalkenyl radical, an unsubstituted or substituted carbocyclic aryl or heteroaryl radical, or a hydroxyl group protecting group ($G_1$ defined above);

$R_4$ represents a hydrogen or an acyl radical or an unsubstituted or substituted straight chain or branched alkyl, alkenyl or akylnyl radical, an unsubstituted or substituted cycloalkyl, heterocycloalkyl, cycloalkenyl or heterocycloalkenyl radical, an unsubstituted or substituted carbocyclic aryl or heteroaryl radical, or a hydroxyl protecting group ($G_1$ defined above);

which comprises condensing a β-lactam of the formula

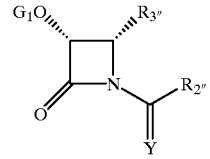

in which

Y and $G_1$ are defined above;

$R_2$, represents a radical $R_2$ as defined above or a protected $R_2$ whenever $R_2$ includes one or more active hydrogens such as hydroxyl, amino, mercapto and carboxyl groups;

R₃, represents a radical as R₃ defined above or a protected R₃ whenever R₃ includes one or more active hydrogens such as hydroxyl, amino, mercapto and carboxyl groups; with a baccatin III derivative of the formula:

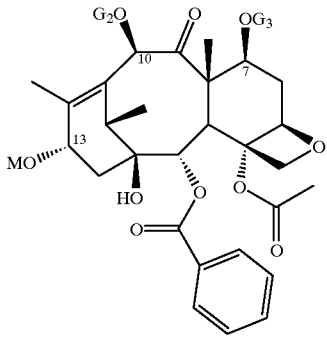

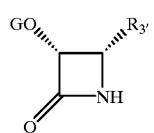

(XI)

wherein G is a hydroxyl protecting group such as triisopropylsilyl (TIPS) and dimethyl(tert-butyl)silyl (TBDMS), and R₃' has been defined hereinabove.

The β-lactams (XI) are readily prepared by using the chrial enolate—imine cyclocondensation method which has been developed in the present inventors laboratory as shown in Scheme 1 (Ojima, I. et al., *Tetrahedron*, 1992, 48, 6985; Ojima, I. et al., *J. Org. Chem.* 1991, 56, 1681). In this preparation the β-lactams (XI) with extremely high enantiomeric purities are obtained in high yields. In Scheme 1, R* is a chiral auxiliary moiety which is (–)-trans-2-phenyl-1-cyclohexyl, TMS is a trimethylsilyl radical, and base is lithium diisopropylamide or lithium hexamethyldisilazide; G and R₃' have been defined hereinabove.

Scheme 1

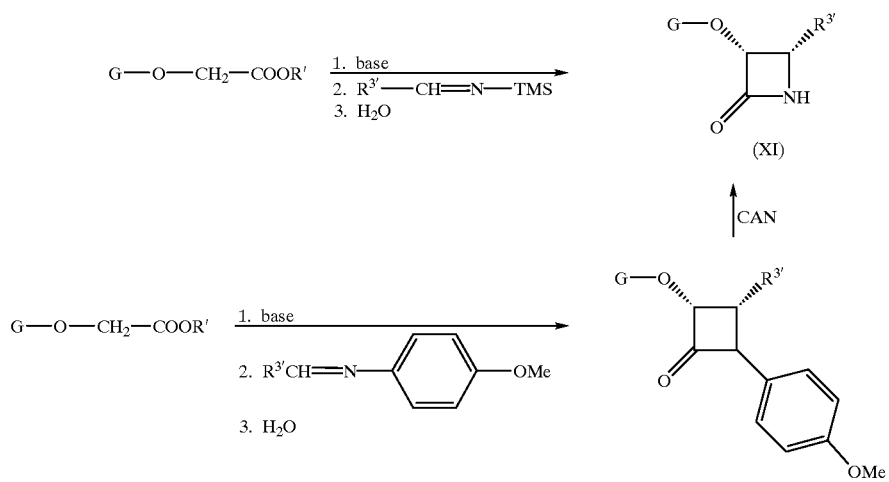

in which

M is an alkali metal or alkaline earth metal atom (ion);

G₂ represents a hydroxyl protecting group (G₁ defined above) or an acyl radical or an unsubstituted or substituted straight chain or branched alkyl, alkenyl or alkynyl radical, an a unsubstituted or substituted cycloalkyl, heterocycloalkyl, cycloalkenyl or heterocycloalkenyl radical, an unsubstituted or substituted carbocyclic aryl or heteroaryl radical;

G₃ represents a hydroxyl group protecting group (G₁ defined above) or an acyl radical or an unsubstituted or substituted straight chain or branched alkyl, alkenyl or alkynyl radical, an unsubstituted or substituted cycloalkyl, heterocycloalkyl, cycloalkenyl or heterocycloalkenyl radical, an unsubstituted or substituted carbocyclic aryl or heteroaryl radical

DETAILED DESCRIPTION OF THE INVENTION

The new β-lactam of the formula (IX) hereinabove are synthesized by modifying the β-lactams of the formula (XI)

The β-lactams (XI) are converted to the 3-hydroxy-β-lactams (XII), followed by protection with ethoxyethyl group (EE) to give the β-lactams (XIII). The β-lactams (XIII) are reacted with chloroformates or formic anhydrides or thiochloroformates or thioformic anhydrides in the presence of a base to yield the β-lactams (XIV) (or thioanalogs thereof) which are used for the coupling with protected 10-deacetylbaccatin III to produce TAXOTÉRE and its analogs. The β-lactams (XIV) are deprotected under weakly acidic conditions to afford the β-lactams (XV) which can serve as very useful intermediates to the β-lactams (XVI) bearing a variety of protecting groups (G₁) and the C-3 position of β-lactam skeleton. The β-lactams (XVI) can also be used for the coupling with a protected 10-deacetylbaccatin III to produce Taxotére and its analogs after deprotection.

In a similar manner, the β-lactams (XVII) are prepared by reacting the β-lactams (XIII) with isocyanates or isothiocyanates in the presence of a base which can be used for the production of other potent anticancer agents of formula (X) in which R₁ represents RR'N-. The β-lactams (XVII) are deprotected under weakly acidic conditions to give the β-lactams (XVIII) which can serve as very useful intermediates to a variety of proteins 3-hydroxyl-β-lactams (XIX). The β-lactams (XVII and XIX) can also be used for the coupling with a protected 10-deacetylbaccatin III to yield a compound of formula (X) in which $R_2$ represents RR'N- after deprotection.

In a manner similar to that described above, the β-lactams (XX) are prepared by reacting the β-lactams (XIII) with N,N-disubstituted carbamoyl halides in the presence of a base. The β-lactams (XX) are deprotected under weakly acidic conditions to give the 3-hydroxy-β-lactams (XXI), which can serve as very useful intermediates to various protected 3-hydroxy-β-lactams (XXII). The β-lactams (XX and XXII) can readily be used for the coupling with a protected baccatin III to afford a compound of formula (X) after deprotection.

The transformations described above are illustrated in Scheme 2. In Scheme 2, X represents a leaving group such as fluoride, chloride, bromide, iodide, tosylate, mesylate and trifluoromesylate. $G_1$ represents a group protecting the hydroxyl function selected from methoxylmethyl (MOM), methoxyethyl (MEM), 1-ethoxyethyl (EE), benzyloxymethyl, (β-trimethylsilylethoxyl) methyl, tetrahydropyranyl, 2,2,2-trichloroethoxylcarbonyl (Troc), benzyloxycarbonyl (CBZ), tertbutoxycarbonyl (t-BOC), 9-fluorenyl methoxycarbonyl (Fmoc), 2,2,2-trichloroethoxymethyl, trimethyl silyl, dimethyl(t-butyl) silyl, diethylmethylsilyl, dimethyl phenylsilyl and diphenylmethylsilyl, acetyl, chloroacetyl, dichloroacetyl, trichloroacetyl and trifluoroacetyl. $R^{2'}$, $R^{3'}$, R, and R' are defined hereinabove.

Scheme 2

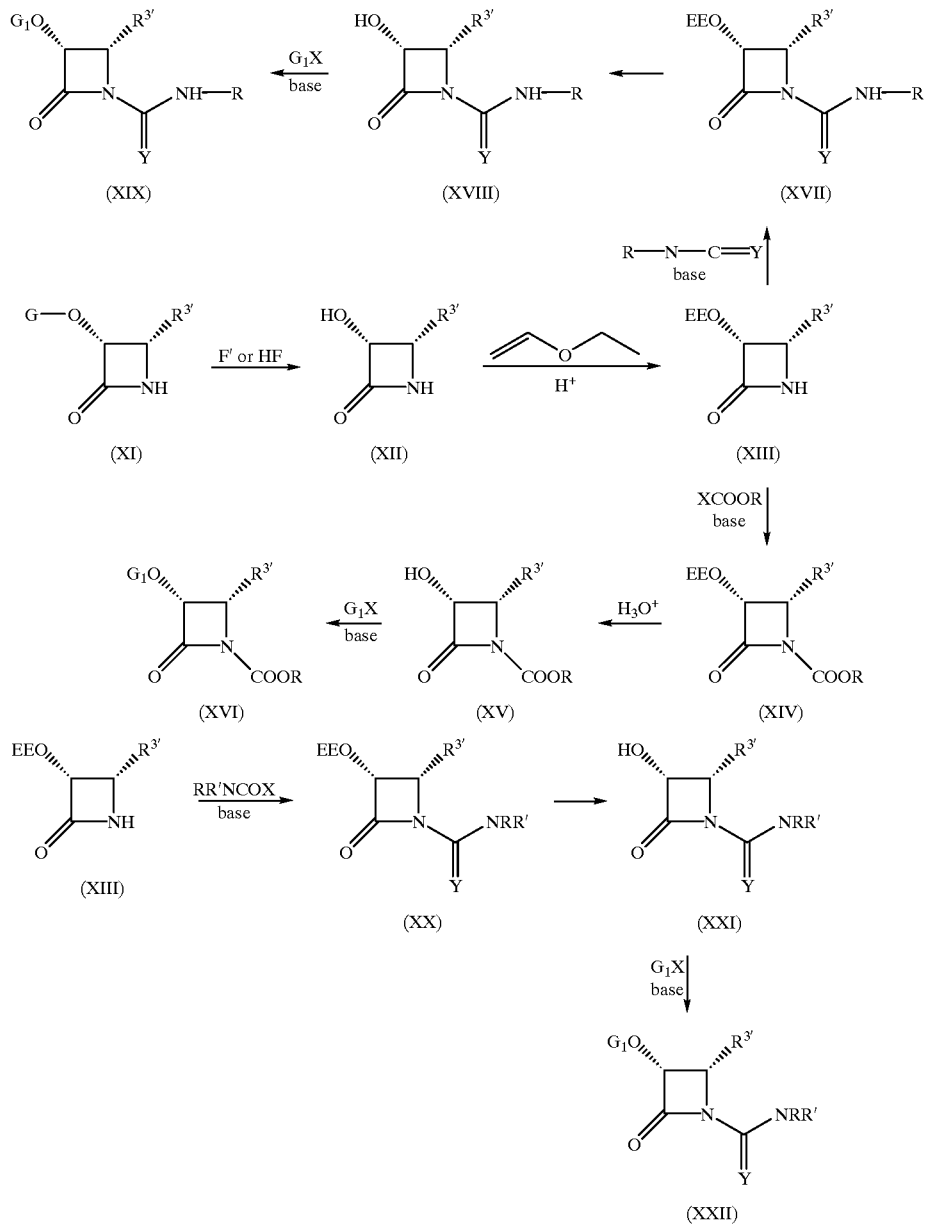

The β-lactams (XIV) and (XVI) are readily used for the coupling with protected baccatin IIIa in the presence of base, followed by deprotection to give TAXOTÈRE and its analogs in high yields (Scheme 3). In a similar manner, the β-lactams (XVII and XIX; with protection of —NH— moiety) and the β-lactams (XX and XXII) can be used for the coupling with protected baccatin IIIa, followed by deprotection to give a compound of formula (X) in which $R_1$ represents $RR^1N$— (Scheme 3).

metal alkoxide of the protected baccatin III at the C-13 hydroxyl group. The alkoxide can readily be generated by reacting the protected baccatin III with an alkali metal or alkaline earth metal base such as sodium hexamethyldisilazide, potassium hexamethyldisilazide, lithium hexamethyldisilazide, sodium diisopropylamide, potassium diisopropylamide, lithium diisopropylamide, sodium hydride, potassium hydride, lithium hydride, calcium hydride, magnesium hydride, in a dry nonprotic organic solvent such as tetrahydrofuran (THF), dioxane,

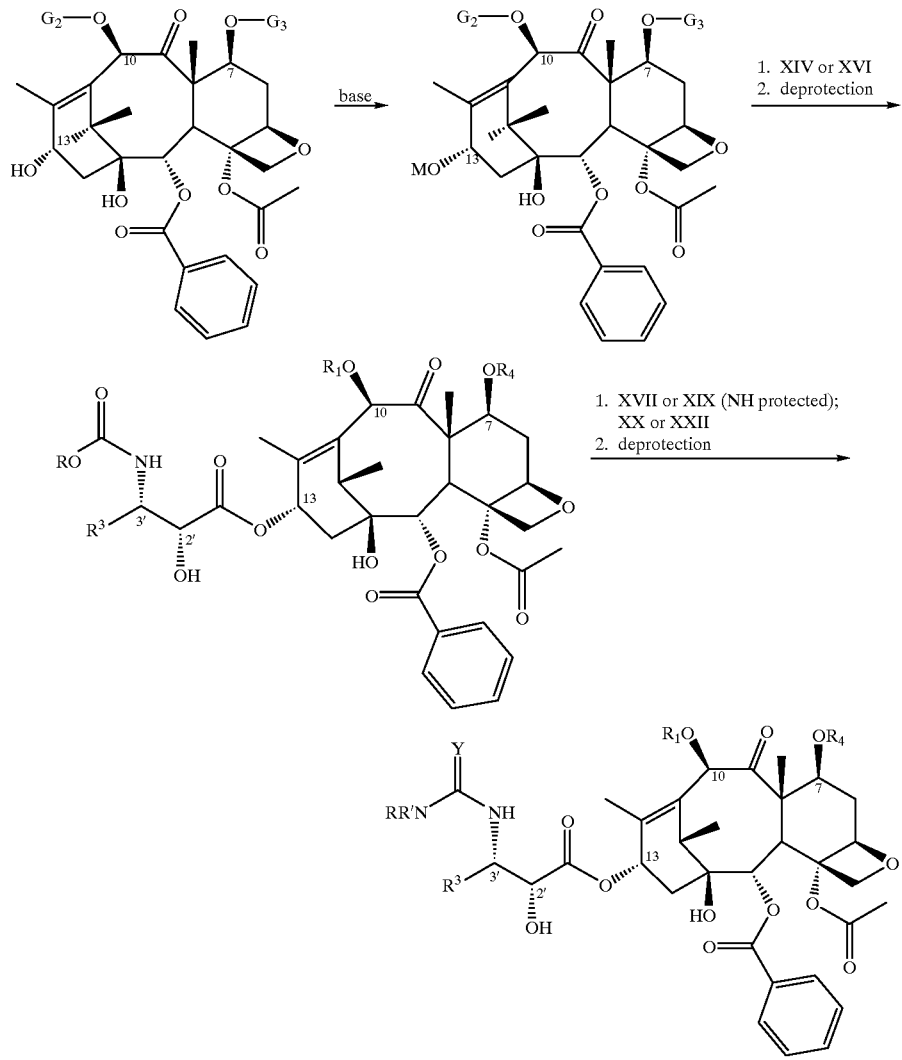

Scheme 3

$G_2$ and $G_3$ represents an hydroxyl protecting group or an acyl radical or an unsubstituted or substituted straight chain or branched alkyl, alkenyl radical, an unsubstituted or substituted cycloalkyl, heterocycloalkyl, cycloalkenyl or heterocycloalkenyl radical, an unsubstituted or substituted carbocyclic aryl or heteroaryl radical.

When $G_2$ and $G_3$ are hydroxyl protecting groups [$G_1$ defined above and 1-ethoxyethoxyl (EE)], these protecting groups can be attached to the hydroxyl groups of 10-deacetylbaccatin III and its analogs by methods which are generally known to those skilled in the art.

The coupling reaction of the protected baccatin III and the β-lactam is carried out via an alkali metal or alkaline earth ether, dimethoxyethane (DME), diglyme, dimethylformamide (DMF), mixtures of these solvents with hexane, toluene, and xylene, in a preferred temperature range from about −100° C. to about 50° C., more preferably at about −78° C. to about 25° C. This reaction is preferably carried out under inert atmosphere such as nitrogen and argon. The amount of the base used for the reaction is preferably approximately equivalent to the amount of the protected baccatin III when soluble bases such as sodium hexamethyldisilazide, potassium hexamethyldisilazide, lithium hexamethyldisilazide, sodium diisopropylamide, potassium diisopropylamide, lithium diisopropylamide are used. The use of a slight excess of the base does not adversely affect the reaction. When heterogeneous bases such as sodium hydride and potassium hydride are used, 5–10 equivalents of the base (to the amount of the protected baccatin III) is preferably employed.

The coupling reaction of the metal alkoxide of the protected baccatin III thus generated with the β-lactam is typically carried out by adding the solution of the β-lactam in a dry organic solvent exemplified above in a preferred temperature range from about −100° C. to 50° C., more preferably at about −35° C. to 25° C. The mixture of reactants is stirred for 15 minutes to 24 hours and the progress and the completion of the reaction is monitored by thin layer chromatography (TLC), for example. When the limiting reactant is completely consumed, the reaction is quenched by addition of a brine. The crude reaction mixture is worked up using the standard isolation procedures which are generally known to those skilled in the art to give the corresponding protected taxoid. The proportion of the β-lactam and the protected baccatin III is in range from 2:1 to 1:2, more preferably approximately 1:1 for purposes of economy and efficiency, but the ratio is not critical for the reaction.

The protecting groups, EE, $G_1$, $G_2$ and $G_3$, can then be removed by using the standard procedures which are generally known to those skilled in the art to give the desired taxane derivatives. For example, EE and triethylsilyl groups can be remove with 0.5N HCl at room temperature for 36 h, and Troc group can be removed with zinc and acetic acid in methanol at 60° C. for 1 hour without disturbing the other functional groups and the skeleton of the taxoid.

The following non-limiting examples are illustrative of the present invention. It should be noted that various changes would be made in the above examples and processes therein without departing from the scope of the present invention. For this reason, it is intended that the illustrative embodiments of the present application should be interpreted as being illustrative and not limiting in any sense.

Examples 1–2

(3R,4S)-3-Triisopropylsilyloxy-4-phenyl-2-azetidinone (1a)

To a solution of 645 mL (4.6 mmol) of diisopropylamine in 10 mL of THF, was added 1.85 mL (4.6 mmol, 2.5M) of n-BuLi at 0° C. The solution was stirred 1 h at 0° C. followed by the addition of 1.5 g (3.8 mmol) of (−) TIPS ester in 15 mL of THF over a 1 h period (using a cannula) at −78° C. The reaction was stirred 2 h at this temperature followed by the addition of 817 mg (4.6 mmol) of N-TMS benzaldimine in 15 mL of THF over a 2 h period at −95° C. The reaction was stirred overnight at this temperature and allowed to slowly warm up at room temperature. The reaction was quenched by addition of sat. $NH_4Cl$. The aqueous layer was extracted with ether. The organic layer was washed with 3% HCl and brine, dried over $MgSO_4$ and concentrated. The crude oil was purified by chromatography on silica gel using 1:5 EtAcO/hexanes to give 1.03 g (84%) of β-lactam as a white solid: Mp 76–77° C.; $[\alpha]_D^{20}$+52.7° (c 1.00, $CHCl_3$); $^1H$ NMR (300 MHz, $CDCl_3$) δ 0.86–0.93 (m, 21H), 4.81 (d, J=4.7 Hz, 1H), 5.17 (dd, J=4.7, 2.6 Hz, 1H), 6.18 (bs, 1H), 7.17–7.35 (m, 5H); $^{13}C$ NMR (75 MHz, $CDCl_3$) δ 11.8, 17.4, 17.5, 59.6, 79.9, 127.9, 128.0, 128.1, 136.4, 170.0; IR (KBr) 3234, 2946–2866, 1760, 1458 cm$^{-1}$.

Anal. Calcd for $C_{18}H_{29}NO_2Si$: C 67.66%, H 9.15%, N 4.38%. Found: C 67.64%, H 9.25%, N 4.44%.

In the same manner, β-lactam 1b was obtained in good yield.

(3R,4S)-3-Triisopropylsilyloxy-4-(2-phenylethenyl)-2-azetidinone (1b)

72%; colorless liquid; $_1H$ NMR (300 MHz, $CDCl_3$) δ 0.98–1.02 (m, 21H), 4.36 (dd, J=4.6, 8.3 Hz, 1H), 5.09 (dd, J=2.3, 4.6 Hz, 1H), 6.29 (dd, J=8.3, 16.0 Hz, 1H ), 6.59 (d, J=16.0 Hz, 1H), 6.83, (bs, 1H), 7.23–7.39 (m, 5H); NMR (75 MHz, $CDCl_3$) δ 11.79, 17.61, 17.66, 58.34, 79.86, 126.05, 126.45, 127.90, 128.56, 134.41, 136.30, 169.69; IR (neat) 3262, 3032, 2944, 2865, 1748, 1672, 1623 cm$^{-1}$.

Anal. Calcd for $C_{20}H_{31}NO_2Si$: C, 69.52; H, 9.04; N, 4.05. Found: C, 69.75; H, 9.02; N, 3.89.

Examples 3–4

To a solution of 2.51 mmol of diisopropylamine in 15 mL of THF was added 2.51 mL of n-butyllithium (2.5M in THF) at −10° C. After 30 min, the lithium diisoipropylamide (LDA) was generated and the solution was cooled to −95° C. A solution of 2.17 mmol of chiral ester in 5 mL of THF was added. After 1 hr, a solution of 2.5 mmol of the appropriate imine in 3 mL of THF was added. The mixture was stirred at −95° C. overnight, and the progress of the reaction was monitored by TLC or $^1H$ NMR. The reaction was quenched with sat. $NH_4Cl$ and THF was removed using a rotary evaporator. Ether (10 mL) was added and the aqueous layer was extracted with ether (10 mL×3). Drying and removal of the solvent gave the crude product which was purified by silica gel column chromatography (hexane/ethyl acetate= 10:1) to afford the corresponding pure β-lactam. The enantiomeric excess was determined by HPLC using a CHIRAL-CEL OD column using n-hexane/i-PrOH (90/10) as the eluent.

(3R,4S)-4-(2-Methylpropyl)-1-(4-methoxyphenyl)-3-triisopropylsilyloxy-2-azetidinone (2a)

87%; pale yellow solid; mp 59–60° C.; $[\alpha]D^{20}$ +60.46° (c 1.26, $CHCl_3$); $^1H$ NMR (300 MHz, $CDCl_3$) δ 0.96 (d, J=6.4 Hz, 3H), 1.03 (d, J=6.4 Hz, 3H), 1.10–1.30 (m, 21H), 1.60–1.68 (m, 1H), 1.70–1.92 (m, 2H), 3.75 (s, 3H), 4.16–4.22 (m, 1H ), 5.06 (d, J=5.1 Hz, 1H), 6.86 (d, J=9.0 Hz, 2H), 7.32 (d, J=9.0 Hz, 2H); $^{13}C$ NMR (75 MHz, $CDCl_3$) δ 12.34, 17.82, 17.91, 22.18, 23.37, 25.34, 35.89, 55.50, 57.33, 76.34, 114.52, 118.73, 131.00, 156.29, 165.58; IR (KBr) 2946, 1742, 1513, 1458, 1249 cm$^{-1}$.

Anal. Calcd for $C_{23}H_{39}NO_3Si$: C, 68.10; H, 9.70; N, 3.45. Found: C 68.26; H, 9.85; N, 3.35.

(3R,4S)-4-(Cyclohexylmethyl)-1-(4-methoxyphenyl)-3-triisopropylsilyloxy-2-azetidinone (2b)

83%; low melting point solid; $[\alpha]D^{20}$ +43.7° (c 0.92, $CHCl_3$); $^1H$ NMR (300 MHz, $CDCl_3$) δ 0.85–1.95 (m, 34H), 3.78 (s, 3H), 4.19–4.25 (m, 1H), 5.05 (d, J=5.1 Hz, 1H), 6.86 (d, J=9.0 Hz, 2H), 7.32 (d, J=9.0 Hz, 2H); $^{13}C$ NMR (75 MHz, $CDC_{13}$) δ 12.15, 17.76, 17.83, 26.12, 26.22, 26.47, 32.84, 34.22, 34.51, 55.36, 56.41, 76.13, 114.30, 118.45, 130.81, 155.99, 165.55; IR (neat) 2925–2865, 1749, 1513, 1464, 1448, 1389, 1246, 1174, 1145, 1128, 939, 882, 828, 684 cm$^{-1}$.

Anal. Calcd for $C_{26}H_{43}NO_3Si$: C, 70.06; H, 9.72; N, 3.14. Found: C, 69.91; H, 9.71; N, 3.02.

Examples 5–6

To a solution of 0.24 mmol of 1-(4-methoxyphenyl)-δ-lactam in $CH_3CN$ (20 mL) was added 0.65 mmol of CAN in 10 mL CH$_3$CN and 20 mL of water in 20 min at −15° C. After stirring for 1 hr, it was diluted with water (20 mL), and the mixture was then extracted with ethyl acetate (15 mL×2). The combined organic layer was washed with NaHSO$_3$ water (7 mL), 5% (10 mL×2), 5% Na$_2$CO$_3$ (10 mL) and brine (5 mL) in sequence. Drying, removal of the solvent in vacuo followed by decolorization with activated charcoal afforded the crude product. It was further purified by silica gel column chromatography (hexanes/ethyl acetate, 3/1) to furnish N-deprotected β-lactam.

(3R,4S)-4-(2-Methylpropyl)-3-triisopropylsilyloxy-2-azetidinone (1c)

83%; yellow oil; $[\alpha]D^{20}$+35.45° (c 1.33, CHCl$_3$); $^1$H NMR (300 MHz, CDCl$_3$) δ 0.93 (d, J=6.6 Hz, 3H), 0.96 (d, J=6.6 Hz, 3H), 1.05–1.25 (m, 22H), 1.52 (m, 1H), 1.67 (m, 1H), 3.78 (m, 1H), 4.96 (dd, J=4.8, 2.4 Hz, 1H), 6.02 (bs, 1H); $^{13}$C NMR (75 MHz, CDCl$_3$) δ 12.12, 17.72, 17.80, 22.29, 23.08, 25.35, 39.08, 54.45, 78.04, 170.00; IR (neat) 3238, 1759, 1465, 1184 cm$^{-1}$.

Anal. Calcd for C$_{16}$H$_{33}$NO$_2$Si: C, 64.16; H,11.1; N, 4.68. Found: C, 64.17; H, 10.96; N, 4.47.

(3R,4S)-4-(Cyclohexylmethyl)-3-triisopropylsilyloxy-2-azetidinone (1d)

85%; yellow oil; $[\alpha]D^{20}$+12.44° (c 1.46, CHCl$_3$); $^1$H NMR (300 MHz, CDCl$_3$) δ 0,97–1.25 (m, 32H), 1.40–1.70 (m, 2H), 3.80 (dt, J=8.4, 4.8 Hz, 1H), 4.95 (dd, J=4.8, 2.4 Hz, 1H), 6.05 (bs, 1H); $^{13}$C NMR (75 MHz, CDCl$_3$) δ 12.06, 17.77, 17.82, 26.16, 26.25, 26.46, 33.15, 33.82, 34.85, 37.72, 53.89, 77.98, 169.98; IR (neat) 3238, 1759, 1465, 1184 cm$^{-1}$.

Anal. Calcd for C$_{19}$H$_{37}$NO$_2$Si: C, 67.20; H, 10.98; N, 4.12. Found: c, 67.40; H, 10.79; N, 3.98.

Examples 7–11

To a solution of 2.6 mmol of 3-triisopropylsilyloxy-4-substituted-2-azetidinone in 20 mL of THF, was added at room temperature 3.1 mmol (1M in THF) of NBu$_4$F. After 5 h, the solvent was evaporated and the crude oil was directly purified by chromatography on silica gel using 5:1 EtAcO/hexanes to afford of 3-hydroxy-4-substituted-2-azetidinone:

(3R,4S)-3-Hydroxy-4-phenyl-2-azetidinone (3a)

100%; white solid; mp 189–190° C.; $[\alpha]D^{20}$+181.6° (c 0.5, CH$_3$OH); $^1$H NMR (300 MHz, CD$_3$OD) δ 4.84 (d, J=4.7 Hz, 1H), 5.04 (d, J=4.7 Hz, 1H), 7.25–7.35 (m, 5H); IR (KBr) 3373, 3252, 1732, 1494 cm$^{-1}$.

Anal. Calcd for C$_9$H$_9$NO$_2$: C 66.25%, H 5.56%, N 8.58%. Found: C 66.42%, H 5.74%, N 8.62%.

(3R,4S)-3-Hydroxy-4-(2-phenylethenyl)-2-azetidinone (3b)

82%; white solid; mp 143–144° C.; $[\alpha]D^{20}$+21.9° (c 1.05, MeOH); $^1$H NMR (300 MHz, CD$_3$OD) δ 4.35 (ddd, J=0.8, 4.7, 7.7 Hz, 1H), 4.93 (d, J=4.7 Hz, 1H), 6.28 (dd, J=7.7, 16.0 Hz, 1H), 7.18–7.43 (m, 5H); $^{13}$C NMR (75 MHz, CD$_3$OD) δ 58.65, 79.63, 126.83, 127.58, 128.88, 129.61, 135.28, 137.96, 172.79; IR (KBr) 3320, 3276, 1754, 1464 cm$^{-1}$.

Anal. Calcd for C$_{11}$H$_{11}$NO$_2$: C, 69.83; H, 5.86; N, 7.40. Found: C, 69.72; H, 5.92; N, 7.24.

(3R,4S)-3-Hydroxy-4-(2-methylpropyl)-2-azetidinone (3c)

94%; white solid; mp 141–142° C.; $[\alpha]D^{20}$+26.6° (c 0.70, MeOH); $^1$H NMR (300 MHz, MeOH-d4) d 0.94 (d, J=6.8 Hz, 3H), 0.97 (d, J=6.8 Hz, 3H), 1.45 (m, 2H), 1.71 (sept, J=6.6 Hz, 1H), 3.75 (m, 1H), 4.79 (d, J=4.7 Hz, 1H); $^{13}$C NMR (75 MHz, MeOH-d4) δ 22.62, 23.48, 26.53, 39.90, 55.47, 77.76, 173.18; IR (KBr) 3274, 3178, 1762, 1685, 1155 cm$^{-1}$.

Anal. Calcd for C$_7$H$_{13}$NO$_2$: C, 58.72; H, 9.15; N, 9.78. Found: C, 58.55; H, 9.41; N, 9.69.

(3R,4S)-4-(Cyclohexylmethyl)-3-hydroxy-2-azetidinone (3d)

92%; white solid; mp 147–148° C.; $[\alpha]D^{20}$+8.73° (c, 0.573, CH$_3$OH); $^1$H NMR (300 MHz, MeOH-d4) δ 0.88–1.82 (m, 13H), 3.78 (m, 1H ), 4.79 (d, J=4.7 Hz, 1H); $^1$H NMR (300 MHz, DMSO-d6) δ 0.86–1.72 (m, 13H), 3.58 (m, 1H), 4.63 (m, 1H), 5.82 (d, J=7.6 Hz, 1H), 8.13 (d, J=5.6, 1H); $^{13}$C NMR (75 MHz, MeOH-d4) δ 27.29, 27.41, 27.48, 34.07, 35.06, 36.11, 38.52, 55.02, 77.65, 173.22; IR (KBr) 3301, 3219, 2915, 2847, 1754, 1694, 1168 cm$^{-1}$.

Anal.Calcd for C$_{10}$H$_{17}$NO$_2$: C, 65.54, H, 9.35, N, 7.64. Found: C, 65.72, H, 9.46, N, 7.42.

(3R,4S)-4-cyclohexyl-3-hydroxy-2-azetidinone (3e)

A suspension of 500 mg (3.06 mmol) of 4-phenyl-3-hydroxy-2-azetidinone 1a and 15 mg of Rh—C in 10 mL of methanol was heated at 90° C. under 800 psi in an autoclave. After 5 days, the hydrogen pressure was released and the catalyst filtrated on celite. Evaporation of the solvent afforded a solid which was recrystallized in ethyl acetate to give 440 mg (85%) of 3e as a white solid: White solid; mp 140–140.5° C.; $[\alpha]_D^{20}$+65.1° (c 0.66, CH$_3$OH); $^1$H NMR (250 MHz, MeOH-d$_4$) δ 0.75–1.10 (m, 2H), 1.12–1.35 (m, 3H), 1.40–2.00 (m, 6H), 3.28 (dd, J=9.7, 4.6 Hz, 1H), 4.81 (d, J=4.6 Hz, 1H); $^1$H NMR (250 MHz, DMSO-d$_6$) δ 0.75–1.00 (m, 2H), 1.10–1.35 (m, 3H), 1.37–1.55 (m, 1H), 1.58–1.85 (m, 5H), 3.10 (dd, J=9.6, 4.7 Hz, 1H), 4.67 (m, 1H), 5.87 (d, J=7.8 Hz, 1H), 8.21 (bs, 1H); $^{13}$C NMR (63 MHz, DMSO-d$_6$) δ 25.08, 25.36, 26.07, 28.83, 29.17, 37.51, 59.04, 76.41, 170.21; IR (KBr) 3312, 3219, 2928, 1726 cm$^{-1}$.

Anal.Calcd for C$_9$H$_{15}$NO$_2$: C, 63.88, H, 8.93, N, 8.28. Found: C, 63.70, H, 9.00, N, 8.06.

Examples 12–16

To a solution of 1.9 mmol of 3-hydroxy-4-substituted-2-azetidinone in 20 mL of THF, was added at 0° C. 3.9 mmol of ethylvinylether. After 2 h, at 0° C., the reaction mixture was diluted with ether and washed with saturated. NaHCO$_3$. The organic layer was dried over Na$_2$CO$_3$, filtered and concentrated to yield of 3-(1-ethoxyethoxy)-4-substituted-2-azetidinone:

(3R,4S)-3-(1-Ethoxyethoxy)-4-phenyl-2-azetidinone (4a)

100%; white solid; mp 78–80° C.; $^1$H NMR (CDCl$_3$) δ [0.98 (d, J=5.4 Hz), 1.05 (d, J=5.4 Hz), 3H], [1.11 (t, J=7.1 Hz), 1.12 (t, J=7.1 Hz), 3H], [3.16–3.26 (m), 3.31–3.42 (m), 3.59–3.69 (m), 2H], [4.47 (q, J=5.4 Hz), 4.68 (q, J=5.4 Hz), 1H], [4.82 (d, J=4.7 Hz), 4.85 (d, J=4.7 Hz), 1H], 5.17–5.21 (m, 1H), 6.42 (bd, 1H), 7.35 (m, 5H); IR (KBr) 3214, 2983, 2933, 1753, 1718, 1456 cm$^{-1}$.

Anal. Calcd for C$_{13}$H$_{17}$NO$_3$: C, 66.36; H, 7.28; N, 5.95. Found: C, 66.46; H, 7.11; N, 5.88.

(3R,4S)-3-(1-Ethoxyethoxy)-4-(2-phenylethenyl)-2-azetidinone (4b)

98%; white solid; mp 98–99° C.; $^1$H NMR (300 MHz, CDCl$_3$) δ [1.17 (t, J=7.1 Hz), 1.18 (t, J=7.1 Hz), 3H], [1.26

(d, J=5.4 Hz), 1.35 (d, J=5.4 Hz), 3H], [3.44–3.52 (m), 3.60–3.68 (m), 3.75–3.82 (m), 2H], 4.41 (dd, J=4.9, 8.5 Hz, 1H), [4.81 (q, J=5.4 Hz), 4.90 (q, J=5.4 Hz), 1H], [5.11 (d, J=4.9 Hz), 5.12 (d, J=4.9 Hz), 1H], 6.01 (bs, 1H), [6.27 (dd, J=15.9 Hz), 6.28 (dd, J=8.5, 15.9 Hz), 1H], [6.61 (d, J=15.9 Hz), 6.63 (d, J=15.9 Hz), 1H], 7.27–7.42 (m, 5H); $^{13}$C NMR (75 MHz, CDCl$_3$) δ 15.04, 20.37, 20.42, 57.22, 57.81, 61.23, 62.22, 78.77, 79.29, 99.50, 99.82, 125.56, 125.79, 126.59, 128.12, 128.65, 134.47, 134.58, 136.15, 168.59, 168.77; IR (KBr) 3310, 3030, 2963, 1770 cm$^{-1}$.

Anal. Calcd for C$_{15}$H$_{19}$NO$_3$: C, 68.94; H, 7.33; N, 5.36. Found: C, 69.13; H, 7.44; N, 5.16.

(3R,4S)-3-(1-Ethoxyethoxy)-4-(2-methylpropyl)-2-azetidinone (4c)

100%; colorless oil: [α]D$^{20}$+20.93° (c 1.72, CHCl$_3$); $^1$H NMR (300 MHz, CDCl$_3$) δ 0.86 (d, J=6.5 Hz, 3H), 0.92 (d, J=6.5 Hz, 3H), 1.17 (t, J=7.0 Hz, 3H), [1.29 (d, J=5.3 Hz), 1.34 (d, J=5.3 Hz), 3H], 1.46 (m, 2H), 1.62 (m, 1H), [3.49 (m), 3.69 (m), 2H)], 3.80 (m, 1H), [4.79 (q, J=5.4 Hz), 4.90 (q, J=5,4 Hz), 1H], 4.87 (m, 1H), 6.78 (bs, 1H ); $^{13}$C NMR (75 MHz, CDCl$_3$) δ 15.08, 20.42, (21.98, 22.06), (23.15, 23.22), 25.35, (39.01, 39.10), (53.35, 53.69), (61.24, 62.24), (77.79, 77.92), (99.75, 100.05), (169.56, 169.65); IR (neat) 3269, 2956, 2871, 1758, 1468, 1382, 1340, 1152, 1115, 1083, 1052, 936, 893 cm$^{-1}$.

(3R,4S)-4-(Cyclohexylmethyl)-3-(1-ethoxyethoxy)-2-azetidinone (4d)

100%; colorless oil; [α]D$^{20}$ 10.92° (c 1.42, CHCl$_3$); $^1$H NMR (100 MHz, CDCl$_3$) δ 0.84–1.71 (m, 13H), 1.16 (t, J=7.0 Hz, 3H), [1.28 (d, J=5.3 Hz), 1.33 (d, J=5.3 Hz), 3H], 3.48 (m, 1H), [3.72 (m), 3.8 (m), 2H], [4.78 (q, J=5.4 Hz), 4.85 (q, J=5.4 Hz), 1H], 4.82 (m, 1H), 6.76 (bs, 1H); $^{13}$C NMR (75 MHz, CDC$_{13}$) δ 14.37, 19.72, 25.30, 25.44, 25.63, (32.02, 32.13), (33.09, 33.17), (34.03, 34.07), (36.98, 37.07), (52.15, 52.49), (60.49, 61.52), (75.97, 76.39), (99.00, 99.35), (168.98, 169.05); IR (neat) 3278, 2924, 2852, 1758, 1448, 1382, 1150, 1114, 1086, 938, 886 cm$^{-1}$.

Anal. Calcd for C$_{14}$H$_{25}$NO$_3$; C, 65.85; H, 9.87; N, 5.49. Found: C, 66.03; H, 9.71; N, 5.30.

(3R,4S)-4-Cyclohexyl-3-(1-ethoxyethoxy)-2-azetidinone (4e)

100%; white solid; mp 87–89° C.; [α]$_D$$^{20}$+83° (c 0.76, CH$_3$OH); $^1$H NMR (250 MHz, CDCl$_3$) δ 0.84 (m, 2H), 1.07–1.34 (m, 9H), 1.66 (m, 6H), 3.32 (m, 1H), [3.42 (q, J=7.7 Hz), 3.54 (q, J=7.7 Hz), 3.65 (q, J=7.7 Hz), 3.74 (q, J=7.7 Hz), 2H], 4.81 (m, 1H), [4.80 (m), 4.90 (q, J=5.2 Hz), 1H], 6.92 (bs, 1H); IR (CHCl$_3$) 3412, 2989, 2931, 1760, 1443, 1155, 1114 cm$^{-1}$.

Anal. Calcd for C$_{13}$H$_{27}$NO$_3$: C, 64.70; H, 9.61; N, 5.80. Found: C, 64.82; H, 9.66; N, 5.64.

Examples 17–27

To a solution of 2.2 mmol of 3-(1-ethoxyethoxy)-4-substituted-2-azetidinone, 5 mg of DMAP, 4.5 mmol of triethylamine in 20 mL of dichloromethane, was added dropwise at 0° C. 3.3 mmol of alkylchloroformate dissolved in 5 mL of dichloromethane. The reaction mixture was stirred overnight at room temperature. The organic layer was washed several times with brine, dried over Na$_2$CO$_3$ and concentrated. The crude solid was purified by chromatography on silica gel to yield N-protected β-lactam:

(3R,4S)-1-Methoxycarbonyl-3-(1-ethoxyethoxy)-4-phenyl-2-azetidinone (5a)

62%; pale yellow oil; [α]D$^{20}$+98.2° (c 1.1, CHCl$_3$); $^1$H NMR (250 MHz, CDCl$_3$) δ [0.97 (d, J=5.4 Hz), 1.08 (d, J=5.4 Hz), 3H], 1.10 (bt, J=7.3 Hz, 3H), [3.21 (dq, J=9.5, 7.1 Hz), 3.32 (q, J=7.1 Hz), 3.64 (dq, J=9.5, 7.1 Hz), 2H], [3.76 (s), 3.77 (s), 3H], [4.48 (q, J =5.4 Hz), 4.69 (q, J=5.4 Hz), 1H], [5.11 (d, J=5.9 Hz), 5.14 (d, J=5.9 Hz), 1H], 5.23 (d, J=5.9 Hz, 1H), 7.34 (m, 5H); $^{13}$C NMR (63 HMz, CDCl$_3$) δ (14.96, 15.07), (19.84, 20.69), 53.59, (60.74, 62.36), (61.14, 61.92), (76.21, 77.21), (99.16, 99.56), (127.73, 128.03, 128.31, 128.36, 128.62, 128.85), (133.41, 133.58), (149.51, 149.57), (165.21, 165.67); IR (neat) 3033, 2979, 2957, 1821, 1738, 1654, 1440, 1336, 1101 cm$^{-1}$.

Anal. Calcd for C$_{15}$H$_{19}$NO$_5$: C, 61.42; H, 6.53; N, 4.78. Found: C, 61.55; H, 6.51; N, 4.90.

(3R,4S)-1-Ethoxycarbonyl-3-(1-ethoxyethoxy)-4-phenyl-2-azetidinone (5b)

82%; colorless oil; [α]D$^{20}$+100.9° (c 1.08, CHCl$_3$); $^1$H NMR (250 MHz, CDCl$_3$) δ [0.95 (d, J=5.4 Hz), 1.06 (d, J=5.4 Hz), 3H], 1.08 (bt, J=7.3 Hz, 3H), [1.19 (t, J=7.1 Hz), 1.20 (t, J=7.1 Hz), 3H], [3.20 (dq, J=9.4, 7.1 Hz), 3.31 (q, J=7.1 Hz), 3.32 (q, J=7.1 Hz), 3.63 (dq, J=9.4, 7.1 Hz), 2H], [4.18 (q, J=7.1 Hz), 4.19 (q, J=7.1 Hz), 2H ], [4.47 (q, J=5.4 Hz), 4.67 (q, J=5.4 Hz), 1H], [5.09 (d, J=5.8 Hz), 5.13 (d, J=5.8 Hz), 1H], 5.21 (d, J=5.8 Hz, 1H), 7.30 (m, 5H); $^{13}$C NMR (63 MHz, CDCl$_3$) δ 14.14, (14.95, 15.07), (19.86, 20.05), (60.76, 62.35), 62.36, (61.14, 61.90), (76.18, 77.20), (99.17, 99.53), (127.73, 128.02, 128.25, 128.30, 128.50, 128.63), (133.59, 133.77), (148.99, 149.05), (165.33, 165.79); IR (neat) 2978, 2934, 1814, 1731, 1646, 1540, 1456, 1323, 1175, 1096 cm$^{-1}$.

Anal. Calcd for C$_{16}$H$_{21}$NO$_5$: C, 62.53; H, 6.89; N, 4.56. Found: C, 62.45; H, 6.63; N, 4.83.

(3R,4S)-1-n-Butoxycarbonyl-3-(1-ethoxyethoxy)-4-phenyl-2-azetidinone (5c)

83%, colorless oil; [α]D$^{20}$+70.4° (c 1.25, CHCl$_3$); $^1$H NMR (250 MHz, CDCl$_3$) δ 0.79 (t, J=7.3 Hz, 3H), [0.94 (d, J=5.1 Hz), 1.07 (d, J=5.1 Hz), 3H], 1.07 (t, J=7.4 Hz, 3H), 1.20 (m, 2H), 1.51 (quint, J=6.7 Hz, 2H ), [3.21 (m), 3.30 (q, J=7.1 Hz), 3.61 (m), 2H], 4.09 (m, 2H), [4.46 (q, J=5.2 Hz), 4.66 (q, J=5.2 Hz), 1H], [5.07 (d, J=5.8 Hz), 5.11 (d, J=5.8 Hz), 1H], 5.19 (d, J=5.8 Hz, 1H), 7.28 (m, 5H); $^{13}$C NMR (63 MHz, CDCl$_3$) δ 13.50, (14.95, 15.29), 18.71, (19.84, 20.05), 30.42, (60.77, 62.33), (61.25, 62.02), 66.51, (76.24, 77.26), (99.17, 99.52), (127.76, 128.03, 128.22, 128.27, 128.50, 128.60), (133.61, 133.80), (148.96, 149.02), (165.40, 165.85); IR (neat) 2961, 2933, 1817, 1732, 1653, 1456, 1394, 1250, 1099 cm$^{-1}$.

Anal. Calcd for C$_{18}$H$_{25}$NO$_5$: C, 64.46; H, 7.51; N, 4.18. Found: C, 64.44; H, 7.57; N, 4.24.

(3R,4S)-1-tert-Butoxycarbonyl-3-(1-ethoxyethoxy)-4-phenyl-2-azetidinone (5d)

83%; white solid; mp 90–91° C.; [α]D$^{20}$+70.4° (c 1.25, CHCl$_3$); $^1$H NMR (250 MHz, CDCl$_3$) δ [0.96 (d, J=5.4 Hz), 1.08 (d, J=5.4 Hz), 3H], [1.09 (t, J=7.0 Hz), 1.10 (t, J=7.0 Hz), 3H], [1.36 (s), 1.37 (s), 9H], [3.23 (dq, J=9.5, 7.1 Hz), 3.32 (q, J=7.1 Hz), 3.65 (dq, J=9.5, 7.1 Hz), 2H ], [4.48 (q, J=5.4 Hz), 4.69 (q, J=5.4 Hz), 1H], [5.03 (d, J=5.8 Hz), 5.07 (d, J=5.8 Hz), 1H], 5.18 (d, J=5.8 Hz, 1H), 7.31 (m, 5H); $^{13}$C NMR (63 MHz, CDCl$_3$) δ (14.98, 15.08), (19.89, 20.10), 27.84, (60.74, 62.32), (61.28, 62.08), (75.91, 76.54), 83.48 (99.10, 99.41), (127.76, 128.07, 128.20, 128.42, 128.85), (133.98, 134.16), 147.56, (165.61, 166.04); IR (CHCl$_3$) 3025, 2982, 2932, 1809, 1725, 1601, 1497, 1331, 1256, 1152 cm$^{-1}$.

Anal. Calcd for $C_{18}H_{25}NO_5$: C, 64.46; H, 7.51; N, 4.18. Found: C, 64.50; H, 7.41; N, 4.17.

(3R,4S)-3-(1-Ethoxyethoxy)-1-phenoxycarbonyl-4-phenyl-2-azetidinone (5e)

79%, white solid; mp 50–52° C.; $[\alpha]_D^{20}$+64.9° (c 0.94, $CHCl_3$); $^1H$ NMR (250 MHz, $CDCl_3$) δ [1.00 (d, J=5.3 Hz), 1.11 (m), 3H], [1.14 (m), 3H], [3.27 (m), 3.35 (q, J=7.1 Hz), 3.70 (m), 2H], [4.54 (q, J=5.3 Hz), 4.74 (q, J=5.3 Hz), 1H], [5.25 (d, J=5.8 Hz), 5.29 (d, J=5.8 Hz), 1H], 5.34 (d, J=5.8 Hz, 1H), 7.03–7.39 (m, 10H); IR ($CDCl_3$) 3028, 2981, 2934, 1815, 1744, 1591, 1486, 1327, 1192 $cm^{-1}$.

Anal. Calcd for $C_{20}H_{21}NO_5$: C, 67.59; H, 5.96; N, 3.94. Found: C, 67.33; H, 6.06; N, 3.75.

(3R,4S)-3-(1-Ethoxyethoxy)-4-phenyl-1-phenylmethoxycarbonyl-2-azetidinone (5f)

44%; white solid; mp 58–60° C.; $[\alpha]_D^{20}$+91.4° (c 1.16, $CHCl_3$); $^1H$ NMR (250 MHz, $CDCl_3$) δ [0.97 (d, J=5.3 Hz), 1.09 (d, J=5.3 Hz), 3H], [1.10 (t, J=7.0 Hz), 1.11 (t, J=7.0 Hz), 3H], [3.23 (dq, J=9.5, 7.1 Hz), 3.33 (q, J=7.1 Hz), 3.66 (dq, J=9.5, 7.1 Hz), 2H], [4.50 (q, J=5.4 Hz), 4.70 (q, J=5.4 Hz), 1H], [5.13 (d, J=5.6 Hz), 5.15 (d, J=5.6 Hz), 1H], [5.19 (s), 5.20 (s), 2H], 5.23 (d, J=5.6 Hz, 1H), 7.21 (m, 2H), 7.26–7.37 (m, 8H); $^{13}C$ NMR (63 MHz, $CDCl_3$) δ (14.99, 15.10), (19.90, 20.10), (60.83, 62.41), (61.64, 62.14), 68.01, (76.31, 77.28), (99.19, 99.53), (127.37, 127.86, 128.07, 128.16, 128.36, 128.52, 128.63, 128.85), (133.49, 133.68), 134.89, (148.72, 148.78), (165.37, 165.81); IR ($CDCl_3$) 3028, 2981, 2934, 1815, 1733, 1604, 1450, 1380, 1004 $cm^{-1}$.

Anal. Calcd for $C_{21}H_{23}NO_5$: C, 68.28; H, 6.28; N, 3.79. Found: C, 68.07; H, 6.43; N, 3.72.

(3R,4S)-1-tert-Butoxycarbonyl-4-cyclohexyl-3-(1-ethoxyethoxy)-2-azetidinone (5q)

91%; colorless oil; $[\alpha]_D^{20}$+62.5° (c 1.12, $CHCl_3$); $^1H$ NMR (250 MHz, $CDCl_3$) δ 1.10—1.28 (m, 6H), 1.15 (t, J=7.0 Hz, 3H), [1.27 (d, J=5.4 Hz), 1.31 (d, J=5.4 Hz), 3H], [1.45 (s), 1.46 (s), 9H], 1.63–1.70 (m, 5H), [3.43 (dq, J=9.2, 7.0 Hz), 3.62 (m), 3.75 (d, J=7.0 Hz), 3.78 (d, J=7.0 Hz), 2H], 3.85 (t, J=6.1 Hz, 1H), [4.78 (q, J=5.4 Hz), 4.88 (m), 1H], [4.85 (d, J=6.1 Hz), 4.86 (d, J=6.1 Hz), 1H]; $^{13}C$ NMR (63 MHz, $CDCl_3$) δ 15.07, (20.25, 20.37), (26.05, 26.14), 26.26, (27.33, 27.95), (29.05, 29.20), (30.04, 30.23), (37.54, 37.64), (61.19, 62.53), (62.06, 62.32), (75.42, 75.85), 83.06, 100.11, 148.72, (166.70, 166.76); IR (neat) 2980, 2931, 2854, 1807, 1725, 1450, 1370, 1329, 1212, 1118 $cm^{-1}$.

Anal. Calcd for $C_{18}H_{31}NO_5$: C, 63.32; H, 9.15; N, 4.10. Found: C, 63.15; H, 8.97; N, 3.96.

(3R,4S)-1-tert-Butoxycarbonyl-3-(1-ethoxyethoxy)-4-(2-phenylethenyl)-2-azetidinone (5h)

86%; white solid; mp 69–73° C.; $^1H$ NMR (100 MHz, $CDCl_3$) δ [1.16 (t, J=7.1 Hz), 1.18 (t, J=7.1 Hz), 3H], [1.25 (d, J=5.4 Hz), 1.36 (d, J=5.4 Hz), 3H], 1.48 (s, 9H), [3.47 (m), 3.62 (m), 3.80 (m), 2H], 4.68 (dd, J=5.8, 8.8 Hz, 1H), [4.82 (q, J=5.4 Hz), 4.91 (q, J=5.4 Hz), 1H], [5.09 (d, J=5.8 Hz), 5.11 (d, J=5.8 Hz), 1H], [6.23 (dd, J=8.8, 15.8 Hz), 6.25 (dd, J=8.8, 15.8 Hz), 1H], [6.72 (d, J=15.8 Hz), 6.73 (d, J=15.8 Hz), 1H], 7.27–7.44 (m, 5H); $^{13}C$ NMR (75 MHz, $CDCl_3$) δ 14.98, 20.31, 27.98, 60.24, 60.85, 61.46, 62.36, 63.58, 83.38, 99.63, 99.87, 122.45, 122.63, 126.69, 128.20, 128.61, 136.15, 136.34, 136.38, 147.74, 147.79, 165.33, 165.53; IR (KBr) 3027, 3020, 2984, 2933, 1809, 1723 $cm^{-1}$.

Anal. Calcd for $C_{20}H_{27}NO_5$: C, 66.46; H, 7.53; N, 3.88. Found: C, 66.60; H, 7.50; N, 3.87.

(3R,4S)-1-tert-Butoxycarbonyl-3-(1-ethoxyethoxy)-4-(2-methylpropyl)-2-azetidinone (5i)

80%; yellow oil; $[\alpha]_D^{20}$+77.45° (c 0.216, $CHCl_3$); $^1H$ NMR (300 MHz, $CDCl_3$) δ 0.89 (d, J=5.7 Hz, 6H), 1.41 (t, J=7.1 Hz, 3H), [1.25 (d, J=5.3 Hz), 1.31 (d, J=5.3 Hz), 3H], 1.45 (s, 9H), 1.51–1.67 (m, 3H), [3.48 (dq, J=9.3, 7.1 Hz), 3.55–3.71 (m, 1H), 3.80 (dq, J =9.3, 7.1 Hz), 2H], 4.08 (q, J=6.1 Hz, 1H), [4.70 (q, J=5.3 Hz), 4.90 (q, J=5.3 Hz), 1H], 4.85 (d, J=6.1 Hz, 1H); $^{13}C$ NMR (75 MHz, $CDCl_3$) δ 14.95, (20.11, 20.28), (22.42, 22.59), 22.70, (24.89, 25.07), 27.83, (37.03, 37.31), (56.14, 56.38), (61.07, 62.27), (75.65, 75.92), 82.98, 99.91, 148.1, (166.1, 165.9); IR (neat) 2931, 2960, 2872, (1790, 1807), (1708, 1726), (1454, 1465), 1332, 1256, 1048, 1158, 996, 955, 857, 834, 770 $cm^{-1}$.

Anal. Calcd for $C_{16}H_{26}NO_5$: C, 60.93; H, 9.27; N, 4.44. Found: C, 61.19; H, 9.41; N, 4.37.

(3R,4S)-1-tert-Butoxycarbonyl-4-cyclohexylmethyl-3-(1-ethoxyethoxy)-2-azetidinone (5j)

93%; yellow oil; $[\alpha]_D^{20}$+75.64° (c 0.78, $CHCl_3$); $^1H$ NMR (300 MHz, $CDCl_3$) δ 0.81–1.74 (m, 13H), 1.19 (t, J=7.1 Hz, 3H), 1.48 (s, 9H), [1.30 (d, J=5.3 Hz), 1.35 (d, J=5.3 Hz), 3H], [3.45 (dq, J=9.3, 7.1 Hz), 3.62–3.71 (m), 3.78 (dq, J=9.3, 7.1 Hz), 2H], 4.01 (m, 1H), [4.81 (q, J=5.3 Hz), 4.91 (q, J=5.3 Hz), 1H], [4.86 (d, J=6.1 Hz), 4.87 (d, J =6.1 Hz), 1H]; $^{13}C$ NMR (75 MHz, $CDCl_3$) δ 15.03, 20.19, 20.36, 26.10, 26.36, 27.91, (33.17, 33.31), (33.35, 33.49), (34.33, 34.58), (35.39, 35.68), (55.77, 55.99), (61.14, 62.21), (75.74, 75.90), 82.96, (99.86, 99.95), 147.96, 166.13; IR (neat 2979, 2923, 2850, 1719, 1807, 1449, 1336, 1154 $cm^{-1}$.

Anal. Calcd. for $C_{19}H_{33}NO_5$: C, 64.20; H, 9.36; N, 3.94. Found: C, 64.00; H, 9.17; N, 4.02.

Examples 28–32

To a solution of 0.5 mmol of 3-(1-ethoxyethoxy)-4-phenyl-2-azetidinone in 6 mL of tetrahydrofuran, was added dropwise at −78° C. 0.6 mmol of n-BuLi. After 5 min, 1 mmol of an isocyanate or an isothiocyanate was added. The reaction mixture was stirred 30 min at −78° C. and quenched by addition of 2 mL sat. $NH_4Cl$ solution. The reaction mixture was diluted with 30 mL of ether and the organic layer was washed several times with brine, dried over $Na_2CO_3$ and concentrated. The crude solid was purified by chromatography on silica gel to yield N-protected β-lactam:

(3R,4S)-3-(1-Ethoxyethoxy)-1-phenylcarbamoyl-4-phenyl-2-azetidinone (7a)

66%; pale yellow solid; mp 152–155° C.; $[\alpha]_D^{20}$+87.8° (c 0.9, $CHCl_3$); $^1H$ NMR (250 MHz, $CDCl_3$) δ[1.07 (d, J=5.4 Hz), 1.13 (d, J=5.4 Hz), 3H], 1.16 (t, J=7.1 Hz, 3H), [3.26 (dq, J=9.5, 7.1 Hz), 3.37 (q, J=7.1 Hz), 3.39 (q, J=7.1 Hz), 3.67 (dq, J=9.5, 7.1 Hz), 2H], [4.53 (q, J=5.4 Hz), 4.72 (q, J=5.4 Hz), 1H], 5.28 (m, 2H), [6.59 (bs), 6.60 (bs), 1H], 7.10–7.55 (m, 10H), 8.68 (bs, 1H); $^{13}C$ NMR (63 MHz, $CDCl_3$) δ (15.04, 15.16), 19.98, 20.11), (60.99, 62.53), 61.80, (76.05, 76.66), (99.34, 99.70), (119.63, 120.69, 124.37, 127.67, 127.95, 128.40, 128.45, 128.67, 128.85, 129.04, 129.12, 130.49), 133.48, (127.03, 137.28), 147.23, 147.29), 168.12, 168.52); IR ($CHCl_3$) 3342, 3017, 2982, 2932, 1773, 1719, 1602, 1548, 1445, 1312, 1224, 1210 $cm^{-1}$.

Anal. Calcd for $C_{20}H_{22}N_2O_4$: C, 67.78; H, 6.26; N, 7.90. Found: C, 67.92; H, 5.98; N, 8.17.

(3R,4S)-1-tert-Butylcarbamoyl-3-(1-ethoxyethoxy)-4-phenyl-2-aze-tidinone (7b)

74%; pale yellow viscous oil; $[\alpha]D^{20}$+144.3° (c 0.7, CHCl$_3$); $^1$H NMR (250 MHz, CDCl$_3$) δ [0.96 (d, J=5.3 Hz), 1.05 (d, J=5.3 Hz), 3H], 1.10 (t, J=7.1 Hz, 3H), [1.33 (s), 1.34 (s), 9H], [3.21 (dq, J=9.3, 7.0 Hz), 3.30 (q, J=7.0 Hz), 3.33 (q, J=7.1 Hz), 3.62 (dq, J=9.1, 7.0 Hz), 2H], [4.46 (q, J=5.4 Hz), 4.66 (q, J=5.4 Hz), 1H), 1H], 5.10–5.19 (m, 2H), [6.59 (bs), 6.60 (bs), 1H], 7.23–7.36 (m, 5H); $^{13}$C NMR (64MHz, CDCl$_3$) δ (14.86, 14.99), (19/75, 19.95), 28.81, 29.30), (60.62, 61.20), 60.80, 62.29), (75.57, 76.76), (98.91, 99.34), (127.07, 127.40, 127.70, 128.17, 128.29, 128.53), (133.71, 133.86), (148.54, 148.59), (167.67, 168.13); IR (CHCl$_3$) 3362, 3035, 2977, 2932, 1767, 1710, 1605, 1537, 1457, 1366, 1320, 1282, 1217, 1100 cm$^{-1}$.

Anal. Calcd for $C_{18}H_{26}N_2O_4$: C, 64.65; H, 7.84; N, 8.38. Found: C, 64.46; H, 7.75; N, 8.39.

(3R,4S)-1-Benzylcarbamoyl-3-(1-ethoxyethoxy)-4-phenyl-2-azetidinone (7c)

50%; pale yellow viscous oil; $[\alpha]D^{20}$ +66.2° (c 0.8, CHCl$_3$); $^1$H NMR (250 MHz, CDCl$_3$) δ [0.99 (d, J=5.5 Hz), 1.08 (d, J=5.5 Hz), 3H], 1.12 (m, 3H), [3.16–3.40 (m), 3.63 (m), 2H], [4.35–4.55 (m), 4.69 (q, J=5.5 Hz), 3H], 5.21 (m, 2H), [7.03 (bs), 7.05 (bs), 1H], 7.32 (m, 10H); $^{13}$C NMR (63 MHz, CDCl$_3$) δ (15.01, 15.14), (19.90, 20.11), 43.83, (60.66, 62.44), (60.75, 61.54), 75.93, 77.04), (99.16, 99.56), (127.25, 127.64, 127.69, 128.17, 127.93, 128.35, 128.55, 128.64, 128.74), (133.95, 133.76), 137.80, 150.02, (167.73, 168.19); IR (CHCl$_3$) 3379, 3090, 3033, 2980, 2930, 1773, 1707, 1604, 1536, 1455, 1319, 1270, 908 cm$^{-1}$.

Anal. Calcd for $C_{21}H_{24}N_2O_4$: C, 68.46; H, 6.57; N, 7.60. Found C, 68.30; H, 6.66; N, 7.51.

(3R,4S)-3-(1-Ethoxyethoxy)-1-ethylcarbamoyl-4-phenyl-2-azetidinone (7d)

63%; pale yellow oil; $[\alpha]D^{20}$ +96.7° (c 0.9, CHCl$_3$); $^1$H NMR (250 MHz, CDCl$_3$) δ [0.96 (d, J=5.3 Hz), 1.04 (d, J=5.3 Hz), 3H], 1.05–1.18 (m, 3H), [3.13–3.39 (m), 3.59 (m), 4H], [4.45 (q, J=5.3 Hz), 4.65 (q, J=5.3 Hz), 1H), 1H], 5.16 (m, 2H), [6.60 (bs), 6.62 (bs), 1H], 7.27 (m, 5H); $^{13}$C NMR (63 MHz, CDCl$_3$) δ 14.98 (19.84 29.93), 34.79, (60.56, 61.35), (60.72, 62.35), (75.91, 77.03), (99.14, 99.54), (127.28, 127.55, 127.85, 128.27, 128.40), (133.74, 133.89), (149.87, 149.93), (167.62, 168.07); IR (CHCl$_3$) 3378, 3035, 2980, 2934, 1774, 1704, 1537, 1455, 1321, 1271, 1112, 1025 cm$^{-1}$.

(3R,4S)-3-(1-Ethoxyethoxy)-1-phenylthiocarbamoyl-4-phenyl-2-aze-tidinone (7e)

82%; yellow solid; mp 108–112° C.; $[\alpha]D^{20}$ +68° (c 1.14, CHCl$_3$); $^1$H NMR (250 MHz, CDCl$_3$) δ [1.02 (d, J=5.5 Hz), 1.11 (d, J=5.5 Hz), 3H], 1.16 (t, J=7.3 Hz, 3H), [3.20–3.44 (m), 3.66 (dq, J=9.4, 7.3 Hz), 2H], [4.52 (q, J=5.5 Hz), 4.72 (q, J=5.5 Hz), 1H], [5.30 (d, J=5.5 Hz), 5.32 (d, J=5.5 Hz), 1H], [5.49 (d, J=5.5 Hz), 5.52 (d, J=5.5 Hz), 1H], 7.36 (m, 8H), 7.67 (d, J=7.8 Hz, 2H), 10.37 (bs, 1H); $^{13}$C NMR (63 MHz, CDCl$_3$) δ (15.04, 15.17), (19.95, 20.13), (60.96, 62.57), (63.92, 64.75), (74.75, 5.84), (99.34, 99.68), (123.43, 126.58, 127.91, 128.28, 128.49, 128.86, 128.91), (133.10, 133.25), (127.36, (166.55, 166.52), (174.812); IR (CHCl$_3$) 3288, 3024, 2983, 1760, 1497, 1385, 1222 cm$^{-1}$.

Examples 33–34

(3R,4S)-1-Morpholinecarbonyl-3-(1-ethoxyethoxy)-4-phenyl-2-azetidinone (7f)

To a solution of 30 mg (0.13 mmol) of 3-(1-ethoxyethoxy)-4-phenyl-2-azetidinone 6 in 2 mL of CH$_2$Cl$_2$, 2 mg of DMAP and 0.05 mL of triethylamine was added at room temperature. After 5 min. 22.9 mg (0.15 mmol) of morpholinecarbonyl chloride was added. The reaction mixture was stirred for 2 h at room temperature. The reaction mixture was diluted with 20 mL of CH$_2$Cl$_2$ and the organic layer was washed two times with brine, dried over Na$_2$CO$_3$ and concentrated. The crude solid product was purified by chromatography on silica gel to yield pure 7f: 87%; pale yellow oil; $^1$H NMR (250 MHz, CDCl$_3$) δ [0.90 (d, J=5.3 Hz), 1.01 (d, J=5.3 Hz) (3H)], [1.04 (t, J=7.1 Hz), 1.18 (t, J=7.1 Hz)] (3H), 3.20 (m, 4H), [3.28 (m), 3.53 (m), 3.67 (m) (2H)], 3.60 (m, 4H), [4.41 (g, J=5.3 Hz), 4.63 (q, J=5.3 Hz) (1H)], [5.07 (d, J=5.8 Hz), 5.08 (d, J=5.8 Hz) (1H], [5.29 (d, J=5.8 Hz), 5.32 (d, J=5.8 hz) (1H], 7.23–7.27 (m, 5H).

Examples 35–53

To a solution of 0.37 mmol of )-EE-β-lactam in 4 mL THF was added 4 mL of 0.5 N HCl. The completion of reaction was monitored by TLC. After 1–3 hr, the reaction mixture was concentrated in vacuo to remove THF. The residue was dissolved in 30 mL ether and washed with 10 mL saturated NaHCO$_3$ solution. The ether layer was washed with brine, dried over anhydrous sodium sulfate, and concentrated in vacuo to give 3-hydroxy-β-lactam:

(3R,4S)-3-Hydroxy-1-methoxycarbonyl-4-phenyl-2-azetidinone (6a)

66%; white solid; mp; 91–92° C. $[\alpha]D^D$ +108° (c 0.63, CHCl$_3$); $^1$H NMR (250 MHz, CDCl$_3$) δ 3.80 (s, 3H), 5.13 (d, J=6.0 Hz, 1H), 5.22 (d, J=6.0 Hz, 1H), 7.25–7.42 (m, 5H); $^{13}$C NMR (63 MHz, CDCl$_3$) δ 53.77, 61.44, 77.33, 127.16, 128.94, 132.65, 149.20, 166.04; IR (CHCl$_3$) 3432, 3024, 2996, 1806, 1730, 1440, 1333, 1188 cm$^{-1}$. MS(FAB) m/z (%) 222 (M+1, 38), 194(29), 164(100).

(3R,4S)-1-Ethoxycarbonyl-3-hydroxy-4-phenyl-2-azetidinone (6b)

59%; white solid; mp 112 113° C.; $[\alpha]D^{20}$ +181° (c 0.97, CHCl$_3$); $^1$H NMR (250 MHz, CDCl$_3$) δ 1.27 (t, J=7.1 Hz, 3H), 4.25 (q, J=7.1 Hz, 2H), 5.14 (d, J=6.0 Hz, 1H), 5.22 (d, J=6.0 Hz, 1H), 7.27–7.39 (m, 5H); $^{13}$C NMR (63 MHz, CDCl$_3$) δ 14.08, 61.36, 63.00, 77.26, 127.08, 128.83, 132.75, 149.08, 165.79; IR (CHCl$_3$) 3605, 3017, 2985, 1815, 1732, 1684, 1396, 1373, 1268, 1020 cm$^{-1}$; MS (FAB) m/z (%) 236 (M+1,98), 208(23), 178(100).

(3R,4S)-1-n-Butoxycarbonyl-3-hydroxy-4-phenyl-2-azetidinone (6c)

69%; white solid; mp 88–89° C.; $[\alpha]D^{20}$ +159.1° (c 0.71, CHCl$_3$); $^1$H NMR (250 MHz, CDCl$_3$) δ 0.78 (t, J=7.3 Hz, 3H), 1.14 (m, 2H), 1.50 (m, 2H), [4.07 (q, J=8.9 Hz), 4.10 (q, J=8.9 Hz), 2H), 5.05 (d, J=5.9 Hz, 1H); 5.11 (d, J=5.9 Hz, 1H), 7.22–7.36 (m, 5H); $^{13}$C NMR (63 MHz, CDCl$_3$) δ 13.44, 18.71, 30.44, 61.54, 66.72, 77.31, 127.21, 128.80, 132.89, 149.15, 166.06; IR (CHCl$_3$) 3562, 3018, 2962, 1813, 1730, 1456, 1395, 1324, 1222, 1099 cm$^{-1}$. MS (FAB) M/z (%) 264(M+1,62), 236(20), 208(40), 206(100).

(3R,4S)-1-tert-Butoxycarbonyl-3-hydroxy-4-phenyl-2-azetidinone (6d)

88%; white solid; mp 131.5–132° C.; $[\alpha]D^{20}$ +173.5° (c 0.98, CHCl$_3$); $^1$H NMR (250 MHz, CDCl$_3$) δ 1.40 (s, 9H), 2.70 (bs, 1H), 5.08 (d, J=5.9 Hz, 1H), 5.14 (d, J=5.9 Hz, 1H), 7.27 (d, J=6.1 Hz, 2H), 7.38 (m, 3H); $^{13}$C NMR (63 MHz, CDCl$_3$) δ 27.87, 61.56, 77.00, 83.85, 127.20, 128.77, 128.82, 133.13, 147.72, 169.49; IR (CHCl$_3$) 3616, 3019, 2976, 1807, 1726, 1601, 1522, 1422, 1333, 1212, 1152 cm$^{-1}$.

Anal. Calcd for C$_{14}$H$_{17}$NO$_4$: C, 63.87; H, 6.51; N, 5.32. Found: C, 63.71; H, 6.38; N, 5.12.

(3R,4S)-3-hydroxy-1-phenoxycarbonyl-4-phenyl-2-azetidinone (6e)

72%; white solid; mp 125–126° C.; [α]D$^{20}$ +107° (c 1.45, CHCl$_3$); $^1$H NMR (250 MHz, CDCl$_3$) δ 5.21 (d, J=6.1 Hz, 1H), 5.34 (d, J=6.1 Hz, 1H), 7.07–7.45 (m, 10H); $^{13}$C NMR (63 MHz, CDCl$_3$) δ 61.83, 73.24, 121.15, 125.46, 126.80, 127.22, 128.09, 128.80, 129.11, 129.30, 132.40, 138.49, 154.05; IR (CHCl$_3$) 3615, 3020, 2976, 1821, 1740, 1506, 1487, 1332, 1219 cm$^{-1}$.

(3R,4S)-1-Benzyloxycarbonyl-3-hydroxy-4-phenyl-2-azetidinone (6f)

85%; white solid; mp 105–106° C.; [α]D$^{20}$ +177° (c 0.6, CHCl$_3$); $^1$H NMR (250 MHz, CDCl$_3$) δ 5.12 (d, J=6.2 Hz, 1H), 5.22 (m, 3H), 7.24–7.40 (m, 10H); $^{13}$C NMR (63 MHz, CDCl$_3$) δ 61.53, 68.30, 77.43, 127.19, 128.13, 128.58, 129.06, 132.55, 134.74, 148.90, 165.92; IR (CHCl$_3$) 3557, 3018, 2924, 1814, 1731, 1383, 1273, 1162, 1004 cm$^{-1}$. MS (FAB) m/z (%) 298(M+1,14), 273(4).

(3R,4S)-1-tert-Butoxycarbonyl-4-cyclohexyl-3-hydroxy-2-azetidinone (6g)

96%; white solid; mp 121–122° C.; [α]D$^{20}$ +78° (c 0.68, CHCl$_3$); $^1$H NMR (250 MHz, CDCl$_3$) δ 1.17–1.75 (m, 11H), 1.48 (s, 9H), 3.83 (t, J+6.5 Hz, 1H), 4.96 (d, J=6.5 Hz, 1H); $^{13}$C NMR (63 MHz, CDCl$_3$) δ 25.87, 25.99, 26.24, 27.96, 29.69, 29.90, 37.45, 63.30, 75.24, 83.43, 148.80, 168.60; IR (CHCl$_3$) 3354, 2931, 2848, 1801, 1724, 1324, 1154 cm$^{-1}$.

(3R,4S)-1-tert-Butoxycarbonyl-3-hydroxy-4-(2-phenylethenyl)-2-azetidinone (6h)

96%; white solid; mp 132–133° C.; [α]D$^{20}$ +122.0° (c 1.1, CHCl$_3$); $^1$H NMR (300 MHz, CDCl$_3$) δ 1.47 (s, 9H), 3.88 (bs, 1H), 4.71 (dd, J=4.8, 8.0 Hz, 1H), 5.07 (d, J=4.8 Hz, 1H), 6.26 (dd, J=8.0, 15.9 Hz, 1H), 6.72 (d, J=15.9 Hz, 1H), 7.24–7.43 (m, (5H); $^{13}$C NMR (75 MHz, CDCl$_3$) δ 27.94, 60.78, 76.58, 83.77, 121.41, 126.75, 128.26, 128.59, 135.94, 136.62, 147.85, 166.95; IR (KBr) 3242, 3039, 2954, 1812, 1726 cm$^{-1}$.

Anal Calcd for C$_{16}$H$_{19}$NO$_4$: C, 66.42; H, 6.62; N, 4.84. Found: C, 66.31; H, 6.71; N, 4.76.

(3R,4S)-1-tert-Butoxycarbonyl-3-hydroxy-4-(2-methylpropyl)-2-aze-tidinone (6i)

98%; pale yellow solid; mp 108° C.; [α]D$^{20}$ +76.14° (c 0.88, CHCl$_3$); $^1$H NMR (300 MHz, CDCl$_3$) δ 0.93 (d, J=6.3 Hz, 6H), 1.48 (s, 9H), 1.62–1.82 (m, 3H), 4.12 (m, 1H), 4.30 (bs, 1H), 4.93 (d, J=5.9 Hz, 1H); $^{13}$C NMR (75 MHz, CDCl$_3$) δ 22.45, 2278, 25.12, 27.96, 36.28, 57.59, 75.39, 83.46, 148.13, 168.00; IR (KBr) 3363, 2960, 2926, 1733, 1763, 1458, 1370, 1350, 1303, 1153 cm$^{-1}$.

Anal. Calcd. for C$_{12}$H$_{21}$NO$_4$: C, 59.24; H, 8.70; N, 5.76. Found: C, 59.47; H, 8.91; N, 5.41.

(3R,4S)-1-tert-Butoxycarbonyl-4-cyclohexylmethyl-3-hydroxy-2-azetidinone (6j)

100%; white solid; mp 105–106° C.; [α]D$^{20}$ +61.89° (c 0.74, CHCl$_3$); $^1$H NMR (300 MHz, CDCl$_3$) δ 0.82–1.84 (m, 13H), 1.50 (s, 9H), 3.82 (bs, 1H), 4.14 (m, 1H), 4.93 (d, J=5.8 Hz, 1H); $^{13}$C NMR (75 MHz, CDCl$_3$) δ 26.12, 26.17, 26.42, 33.20, 33.47, 3359, 34.71, 28.00, 57.13, 75.49, 83.47, 148.08, 167.57; IR (KBr) 3442, 2921, 2850, 1797, 1682, 1447, 1354, 1342, 1159 cm$^{-1}$.

Anal. Calcd. for C$_{15}$H$_{25}$NO$_4$: C, 63.58; H, 8.89; N, 4.94. Found: C, 63.76; H, 8.72; N, 4.68.

(3R,4S)-3-hydroxy-4-phenyl-1-phenylcarbamoyl-2-azetidinone (8a)

88%; white solid; mp 197–200° C.; [α]D$^{20}$ +206.4° (c 1.26, CHCl$_3$); $^1$H NMR (250 MHz, CD$_3$COCD$_3$) δ 5.39–5.47 (m, 2H), 7.07–7.60 (m, 10H), 8.80 (bs, 1H); $^{13}$C NMR (63 MHz, CD$_3$COCD$_3$) δ 61.98, 78.06, 119.85, 124.31, 128.11, 128.31, 128.60, 129.48, 135.31, 138.43, 148.17, 169.76; IR (CHCl$_3$) 3343, 3018, 2975, 1772, 1603, 1548, 1447, 1362, 1219, 1045 cm$^{-1}$; MS (FAB) m/z(%) 283(2), 263(33) 207(22), 143(100).

(3R,4S)-1-tert-Butylcarbamoyl-3-hydroxy-4-phenyl-2-azetidinone (8b)

89%; white solid; mp 148–151° C.; [α]D$^{20}$ +160.9° (c 1.28, CHCl$_3$); $^1$H NMR (250 MHz, CDCl$_3$) δ 1.35 (s, 9H), 3.16 (bs, 1H), 4.97 (d, J=5.5 Hz, 1H), 5.11 (d, J=5.5 Hz, 1H), 6.60 (bs, 1), 7.19 14 7.38 (m, 5H); $^{13}$C NMR (63 MHz, CDCl$_3$) δ 28.84, 51.53, 60.74, 76.61, 127.00, 128.61, 128.70, 133.13, 148.78, 168.30; IR (CHCl$_3$) 3362, 3018, 2975, 1767, 1710, 1533, 1422, 1318, 1216, 1045 cm$^{-1}$. Anal. Calcd for C$_{14}$H$_{18}$N$_2$O$_3$: C, 64.11; H, 6.92; N, 10.68. Found: C, 64.10; H, 7.08; N, 10.49.

(3R,4S)-1-Benzylcarbamoyl-3-hydroxy-4-phenyl-2-azetidinone (8c)

63%; white solid; mp 165–168° C.; [α]D$^{20}$ +139° (c 0.64, CHCl$_3$); $^1$H NMR (300 MHz, CDCl$_3$) δ 3.10 (bs, 1H), 4.43 (dd, J=15.2, 5.8 Hz, 1H), 4.50 (dd, J=15.2, 5.8 Hz, 1H), 5.03 (d, J=5.6 Hz, 1H), 5.20 (d, J=5.6 Hz, 1H), 7.06 (t, J=5.8 Hz, 1H), 7.23–7.33 (m, 10H); $^{13}$C NMR (63 MHz, CDCl$_3$) δ 43.79, 61.01, 76.94, 127.13, 127.73, 128.80, 128.86, 132.94, 137.59, 150.15, 168.34; IR (CHCl$_3$) 3364, 3028, 2925, 1771, 1704, 1537, 1455, 1361, 1219, 1190, 987 cm$^{-1}$.

Anal. Calcd for C$_7$H$_{16}$N$_2$O$_3$: C$_1$ 68.91; H, 5.44; N. 9.45. Found: C$_1$ 68.89; H. 5.66; N, 9.34.

(3R,4S)-1-Ethylcarbamoyl-3-hydroxy-4-phenyl-2-azetidinone (8d)

55%; white solid; mp 141–42° C.; [α]D$^{20}$ +211.4° (c 0.44, CHCl$_3$); $^1$H NMr (250 MHz, CDCl$_3$) δ 1.19 (t, J=7.2 Hz, 3H), 3.34 (qd, J=7.2, 1.6 Hz, 2H), 5.09 (d, J=5.6 Hz, 1H), 5.27 (d, J=5.6 Hz, 1H), 6.63 (bt, J=1.6 Hz, 1H), 7.23–7.44 (m, 5H); $^{13}$C NMR (63 MHz, CDCl$_3$) δ 15.04, 34.94, 60.77, 76.98, 127.00, 128.92, 129.06, 132.83, 149.96, 167.98; IR (CHCl$_3$) 3381, 3018, 2990, 1770, 1732, 1651, 1589, 1422, 1298, 1210, 1045 cm$^{-1}$.

(3R,4S)-3-(1-Hydroxy)-1-phenylthiocarbamoyl-4-phenyl-2-azetidinone (8e)

78%; yellow solid; mp 85–88° C.; [α]D$^{20}$ +156.7° (c, 0.67, CHCl$_3$); $^1$H NMR (300 MHz, CDCl$_3$) δ 5.16 ( d, J=5.8 Hz, 1H), 5.53 (d, J=5.8 Hz, 1H), 7.31–7.44 (m, 8H), 7.66 (d, J=7.8 Hz, 2H), 10.33 (bs, 1); $^{13}$C NMR (63 MHz, CDCl$_3$) δ 63.97, 75.72, 123.29, 126.49, 127.27, 128.77, 132,49, 137.26, 174,07; IR (CHCl$_3$) 3553, 3295, 3048, 2949, 1760, 1601, 1384, 1313, cm$^{-1}$; MS (FAB) m/z (%) 299(M+1, 46), 179(100).

(3R,4S)-1-(Morpholinecarbonyl)-3-hydroxy-4-phenyl-2-azetidinone (8f)

83%; white solid; mp 55–57° C.; $^1$H NMR (250 MHz, CDCl$_3$) δ 3.05 (bs, 1H), 3.56–3.78 (m, 8H), 5.00 (d, J=5.9 Hz, 1H), 5.38 (d, J=5.9 Hz, 1H), 7.24–7.40 (m, 5H).

(3R,4S)-1-(N,N-Dimethylcarbamoyl)-3-hydroxy-4-phenyl-2-azetidinone (8g)

88%; white crystal; mp 123–125° C.; $_1$H NMR (250 HMz, CDCl$_3$) δ 3.06 (bs, 6H), 4.98 (d, J=5.9 Hz, 1H), 5.35 (d, J=5.9 Hz, 1H), 7.29–7.39 (m, 5H).

(3R,4S)-1-tert-Butoxycarbonyl-4-phenyl-3-(1,1,1-trichloroethoxycarbonyloxy)-2-azetidinone (9a)

To a solution of 99 mg (0.38 mmol) of 1-tert-butylcarbonyl-3-hyrdroxy-4-phenyl-2-azetidione, 5 mg of DMAP and 263 mL (2 mmol) of triethylamine in 5 mL of cihloromethane, was added at 0° C. 105 mL (0.8 mmol) of 1,1,1,-trichloroethyl-chloroformate. The reaction mixture was stirred overnight at room temperature. The organic layer was washed several times with brine, dried over MgSO$_4$ and concentrated. The crude solid was purified by chromatography on silica gel to yield 65 mg (40%) of O-protected β-lactam: White solid; mp 122–124° C.; [α]D$^{20}$ +28° (c, 0.5, CHCl$_3$); $^1$H NMR (250 MHz, CDCl$_3$) δ 1.39 (s, 9H), 4.43 (d, J=11.7 Hz, 1H), 4.55 (d, J=11.7 Hz, 1H), 5.28 (d, J=5.5 Hz, 1H), 5.76 (d, J=5.5 Hz, 1H), 7.30 (m, 5H); $^{13}$C NMR (63 MHz, CDCl$_3$) δ 27.81, 60.80, 77.03, 78.76, 84.40, 127.73, 128.58, 129.09, 131.55, 147.71, 152.17, 160.34; IR (CHCl$_3$) 3016, 2976, 1819, 1771, 1732, 1683, 1244 cm$^{-1}$.

Anal. Calcd for C$_{17}$H$_{18}$Cl$_3$NO$_6$: C, 46.54; H, 4.14; N, 3.19. Found: C, 46.33; H, 4.34; N, 3.33.

(3R,4S)-3-Acetoxy-1-tert-butoxycarbonyl-4-phenl-2-azetidinone (9b)

To a solution of 82 mg (0.3 mmol) of 1-tert-butylcarbonyl-3-hydroxy-4-phenyl-2-azetidinone, 5 mg of DMAP and 210 mL (1.5 mmol) of triethylamine in 5 mL of dichloromethane, was added at 0° C. 58 mL (0.7 mmol) of acetic anhydride. The reaction mixtrue was stirred overnight at room temeprtaure. The organic layer was washed several times with brine, dried over MgSO$_4$ and conecntrated. The cude solid was purified by chromatography on silica gel to yield 71 mg (75%) of O-acetyl β-lactam: White solid; mp 63–64° C.; [α]D$^{20}$ +32.1° (c 0.81, CHCl$_3$); $^1$H NMR (250 MHz, CDCl$_3$) δ 1.37 (s, 9H), 1.65 (s, 3H), 5.22 (d, J=5.5 Hz, 1H), 5.83 (d, J=5.5 Hz, 1H), 7.23 –7.33 (m, 5H); $^{13}$C NMR (63 MHz, CDCl$_3$) δ 19.71, 27.81, 60.84, 75.94, 84.07, 127.43, 128.31, 128.67, 132.44, 147.25, 162,39, 168.83; IR (CHCl$_3$) 3026, 2984, 1815, 1752, 1497, 1371, 1286, 1224, 1152, 1024 cm$^{-1}$.

Anal. Calcd for C$_{16}$H$_{19}$NO$_5$: C, 62.94; H, 6.27; N, 4.59. Found: C, 63.17; H, 6.14; N, 4.52.

Example 54

To a suspension of NaH (35 mg in 1.0 mL of DME), was added at –10° C., a solution of 133 mg (0.15 mmol) of 7,10-ditroc-10-deacetylbaccatin III and 100 mg (0.30 mmol) of 5d in 1.5 mL of DME. The reaction was monitored by TLC and quenched at –8° C. by addition of brine. The aqueous layer was extracted with dichloromethane. The combined organic layers were washed with brine, dried over Na$_2$CO$_3$ and concentrated. The crude oil was purified by chromatography on silica gel using AcOET/hexanes (1/2) as the eluant to give 148 mg of the ocupling product 2'-EE-7,10-ditroc-Taxotère as a white solid (81% yield; 90% conversion yield) and 12 mg of 7,10-ditroc-10-deacetylbaccatin III (10% recovery).

The EE protecting group was removed by stirring at room temperature 90 mg of 2'-EE-7,10-ditroc-Taxotère in 3 mL of THF and 2 mL of 0.5 N HCl for 1 hr. The reaction mixture was diluted with dichloromethane. The organic pahse was washed with sat. NaHCO$_3$ sol., brine dried over MgSO$_4$ and concentrated. The crude oil was purified by chromatography on silica gel using AcOET/hexanes (1/2) as the eluant to give 60 mg (71%) of 2'-OH-7,10-ditroc-Taxotère as a white solid; Mp 154–155° C.; [α]D$^{20}$ –38° (c 0.74, CHCl$_3$); $^1$H NMR (250 MHz, CDCl$_3$) δ 1.19 (s, 3H), 1.26 (s, 3H), 1.35 (s, 9H), 1.85 (s, 3H), 1.95 (s, 3H), 2.04 (m, 1H), 2.34 (m, 2H), 2.39 (s, 3H), 2.62 (m, 1H), 3.90 (d, J=6.4 Hz, 1H), 4.17 (d, J=8.4 Hz, 1H), 4.32 (d, J=8.4 Hz, 1H), 4.60 (d, J=11.9 Hz, 1H), 4.64 (m, 1H), 4.78 (s, 2H), 4.91 (d, J=11.9 Hz, 1H), 4.95 (m, 1H), 5.26 (bd, J=8.7 Hz, 1H), 5.46 (bd, J=9.2 Hz, 1H), 5,54 (dd, J=10.4, 7.1 Hz, 1H), 5.69 (d, J=6.8 Hz, 1H), 6.21 (bt, J=8.7 Hz, 1H), 6.24 (s, 1H), 7.32–7.35 (m, 5H), 7.50 (t, J=7.5 Hz, 2H), 7.62 (t, J=7.3 Hz, 1H), 8.10 (d, J=7.5 Hz, 2H); $^{13}$C NMR (63 MHz, CDCl$_3$) δ 10.69, 14.63, 20.91, 22.47, 26.25, 28.14, 33.20, 35.21, 43.07 46.91, 56.14, 7217, 73.50, 74.10, 76.48, 77.33, 77.51, 78.55, 79.08, 80.23, 80.67, 83.61, 94.11, 126.70, 128.06, 128.70, 128.88, 130.12, 131.91, 133.79, 138.20, 142.48, 153.12, 153.17, 155.36, 166.82, 170.33, 172.78, 200.70; IR (CHCl$_3$) 3572, 3444, 3034, 2979, 1759, 1737, 1724, 1490, 1450, 1376, 1106 cm$^{-1}$.

Example 55

To a solution of 90 mg (0.1 mmol) of 7,10-ditroc-10-deacetylbaccatin III and 47 mg (0.14 mmol) of 5d in 5 mL of THF, was added at –30° C. 110 mL (0.11 mmol, 1M in THF) of sodium hexamethyldisilazide. The reaction was monitored by TLC and quenched by addition of brine. The aqueous layer was extracted with dichloromethane. The combined organic layers were washed with brine, dried over Na$_2$CO$_3$ and concentrated. The crude oil was purified by chromatography on silica gel using AcOET/hexanes (1/2) as the eluant to give 117 mg of hte ocupling product 2'-EE-7,10-ditroc-Taxotère as a white solid (94%). All physical and spectral data are identical with those of 2'-EE-7,10-ditroc-Taxotère described in Example 54.

The Troc protecting group was removed by stirring at 60° C. 50 mg of 7,10-ditroc-Taxotère in 1 mL of MeOH and 1 mL of AcOH in presence of 150 mg of zinc for 1 hr. The reaction mixture was filtrated and diluted with dichloromethane. The organic phase was washed with sat. NaHCO$_3$ sol., brine dried over MgSO$_4$ and concentrated. The crude oil was purified by chromatography on silica gel using AcOET/hexanes (1/1) as the eluant to give 28 mg (80%) of Taxotère as a white solid: [α]$_D^{20}$ –34° (c 0.7, EtOH); $^1$H NMR (250 MHz, CDCl$_3$) δ 1.13 (s, 3H), 1.26 (s, 3H), 1.35 (s, 9H), 1.80 (s, 3H), 1,85 (m, 1H), 1.90 (s, 3H), 2.24 (m, 2H), 2.39 (s, 3H), 2.55 (m, 1H), 2.62 (m, 1H), 3.53 (s, 1H), 3.92 (d, J=7.0 Hz, 1H), 4,18 (d, J=8.4 Hz, 1H), 4.22 (m, 1H), 4.32 (d, J=8.4 Hz, 1H0, 4.66 (d, J=6.9 hz, 1H), 6.19 (bt, J=8.1 Hz, 1H), 7.32–7.35 (m, 5H), 7.50 (t, J=7.5 Hz, 2H), 7.62 (t, J=7.3 Hz, 1H), 8.10 (d, J=7.5 Hz, 2H). These data are consistent with those reported for Taxotère by Mangatal, L. et al. (Ref. Mangatal, L.; Adeline, M. T.; Geénard, D.; Geéritte-Voegelein, F.; Potier, P. Tetrahedron 1989, 45, 4177.)

Although the invention has been described in conjunction with specific embodiments, it is evident that many alternatives and variations will be apparent to those skilled in the art in light of the foregoing description. Accordingly, the invention is intended to embrace all of the appended claims. The above references are hereby incorporated by reference.

What is claimed is:

1. A process for the preparation of a metallized baccatin III derivative of the formula

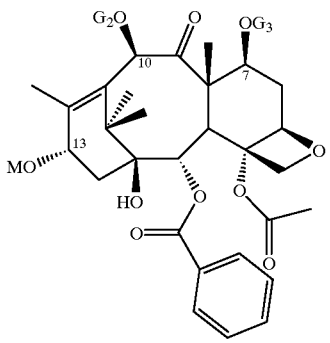

wherein

M is an alkali metal or alkaline earth metal atom (ion), comprising metallizing the corresponding baccatin III compound by reacting said baccatin III compound with a coupling agent, wherein said coupling agent is an alkali metal alkyl disilazide; and wherein $G_2$ is acetyl, or a hydroxyl protecting group; and $G_3$ is a hydroxyl protecting group.

2. The process according to claim 1, further comprising reacting a β-lactam with said metallized baccatin III derivative to form a taxane.

3. The process of claim 1, wherein:

$G_2$ is acetyl, or 2,2,2-trichloroethoxy-carbonyl (Troc);

$G_3$ is 2,2,2-trichloroethoxycarbonyl (troc), or a silyl group selected from trimethylsilyl, triethylsilyl, tripropylsilyl, dimethylethylsilyl, dimethylphenylsilyl, dimethyl(t-butyl)silyl, diethylmethylsilyl, and diphenylmethylsilyl.

4. The process according to claim 2, further comprising deprotecting one or more hydroxyl groups on the taxane.

5. The process according to claim 4, wherein deprotection is accomplished with zinc, acetic acid, and methanol.

6. The process according to claim 5, wherein deprotection is accomplished in approximately 1 hour at 60° C.

7. The process according to any one of claims 1, 2, 3, or 4 wherein the alkali metal alkyl disilazide is at least one compound selected from LiHMDS, NaHMDS, and KHMDS.

8. The process according to claim 7, wherein the at least one compound is NaHMDS.

* * * * *

UNITED STATES PATENT AND TRADEMARK OFFICE
CERTIFICATE OF CORRECTION

PATENT NO. : 6,218,553 B1
DATED : April 17, 2001
INVENTOR(S) : Iwao Ojima

It is certified that error appears in the above-identified patent and that said Letters Patent is hereby corrected as shown below:

<u>Title page,</u>
Item [62] in the Related U.S. Application Data,
Line 2, delete "abandoned" and insert -- issued as U.S. Patent No. 6,187,916, --.
Line 3, "08/363,610" should read -- 08/383,610 --.

Item [57] in the ABSTRACT,
Lines 7, 9, 12 and 15, "Taxotére" should read -- Taxotère --.

<u>Column 28, claim 3,</u>
Line 11, "(troc)" should read -- (Troc) --.

Signed and Sealed this

Twenty-sixth Day of February, 2002

Attest:

Attesting Officer

JAMES E. ROGAN
*Director of the United States Patent and Trademark Office*

UNITED STATES PATENT AND TRADEMARK OFFICE
CERTIFICATE OF CORRECTION

PATENT NO. : 6,218,553 B1 Page 1 of 1
DATED : April 17, 2001
INVENTOR(S) : Iwao Ojima It is certified that error appears in the above-identified patent and that said Letters Patent is hereby corrected as shown below:

<u>Column 1,</u>
Line 17, after "process.", insert -- This work was partially supported by a research grant from the U.S. National Institutes of Health (GM042798). --.

Signed and Sealed this

Fourth Day of April, 2006

JON W. DUDAS
*Director of the United States Patent and Trademark Office*